US012612428B2

(12) United States Patent
Kreuzer

(10) Patent No.: US 12,612,428 B2
(45) Date of Patent: Apr. 28, 2026

(54) PROCESS FOR SOLID-PHASE PEPTIDE SYNTHESIS AND DEVICE

(71) Applicant: Oliver Johannes Kreuzer, Potsdam (DE)

(72) Inventor: Oliver Johannes Kreuzer, Potsdam (DE)

( * ) Notice: Subject to any disclaimer, the term of this patent is extended or adjusted under 35 U.S.C. 154(b) by 1133 days.

(21) Appl. No.: 17/421,672

(22) PCT Filed: Feb. 4, 2020

(86) PCT No.: PCT/EP2020/052681
§ 371 (c)(1),
(2) Date: Jul. 8, 2021

(87) PCT Pub. No.: WO2020/148463
PCT Pub. Date: Jul. 23, 2020

(65) Prior Publication Data
US 2022/0064208 A1     Mar. 3, 2022

(30) Foreign Application Priority Data

Jan. 15, 2019     (DE) ..................... 10 2019 100 924.3

(51) Int. Cl.
*C07K 1/04*          (2006.01)
*B01J 19/10*         (2006.01)
*C07K 1/00*          (2006.01)

(52) U.S. Cl.
CPC .............. *C07K 1/045* (2013.01); *B01J 19/10* (2013.01); *C07K 1/00* (2013.01); *B01J 2219/00932* (2013.01)

(58) Field of Classification Search
None
See application file for complete search history.

(56) References Cited

U.S. PATENT DOCUMENTS

| | | | |
|---|---|---|---|
| 3,867,269 A | 2/1975 | Shimonishi et al. | |
| 6,277,332 B1 | 8/2001 | Sucholeiki | |
| 2012/0132572 A1 | 5/2012 | Christensen | |
| 2013/0310265 A1* | 11/2013 | Menegatti ................ | C07K 7/64 506/30 |

FOREIGN PATENT DOCUMENTS

| | | | | |
|---|---|---|---|---|
| CN | 203569010 U | 4/2014 | | |
| CN | 209052610 U | 7/2019 | | |
| DE | 4006349 A1 | 9/1991 | | |
| DE | 10131088 A1 | 1/2003 | | |
| WO | WO-2012090150 A2 * | 7/2012 | ............. | A61K 47/62 |

OTHER PUBLICATIONS

Adamson et al., Int. J. Peptide Protein Res. 22:560-564 (1983) (Year: 1983).*
Anuradha et al, Tetrahedron 51:5675-5680 (1995) (Year: 1995).*
Wolczanski, Grzegorz et al., "A faster solid phase peptide synthesis method us8ing ultrasonic agitation", Tetrahedron Letters, vol. 60, No. 28, pp. 1814-1818, Jun. 1, 2019, Elsevier Ltd.
Perez, J. Manuel et al., "The Use of Power Ultrasound Coupled with Magnetic Separation for the Solid Phase Synthesis of Compound Libraries", Bioorganic & Medicinal Chemistry Letters, vol. 10, No. 2, pp. 171-174, May 11, 2017, Pergamon, Amsterdam, NL.
Merlino, Franceso et al., "Boosting Fmoc Solid-Phase Peptide Synthesis by Ultrasonication", Organic Letters, vol. 21, No. 16, pp. 6378-6382, Jul. 30, 2019.
International Search Report, issued May 26, 2020 in International Application No. PCT/EP2020/052681.
Electronic Supplementary Information (ESI) for Wolczanski et al., "A faster solid phase peptide synthesis method using ultrasonic agitation,".
Supporting Information for Merlino et al., "Boosting Fmoc Solid-Phase Peptide Synthesis by Ultrasonication,".
Office Action issued Feb. 14, 2025, in Japanese Patent Application No. 2021-540848.

* cited by examiner

*Primary Examiner* — Thea D' Ambrosio
(74) *Attorney, Agent, or Firm* — Wood, Phillips, Katz, Clark & Mortimer

(57) ABSTRACT

A method for carrying out solid-phase peptide synthesis, to an automated parallel solid-phase peptide synthesis, and to a device designed to carry out such a method. Ultrasound with a frequency of more than 25 kHz acts at least intermittently during the method on the reaction medium in which the solid-phase peptide synthesis takes place.

27 Claims, 13 Drawing Sheets

Specification includes a Sequence Listing.

Purity

| No. UV_VIS_1 | Time UV_VIS_1 min | Area UV_VIS_1 mAU*min | Height UV_VIS_1 mAU | Rel.Area UV_VIS_1 % |
|---|---|---|---|---|
| 1 | 8.37 | 11.189 | 136.417 | 1.67 |
| 2 | 8.60 | 18.085 | 186.367 | 2.70 |
| 3 | 9.07 | 8.774 | 130.405 | 1.31 |
| 4 | 9.25 | 555.623 | 2155.954 | 83.05 |
| 5 | 9.77 | 68.185 | 509.910 | 10.19 |
| 6 | 10.19 | 7.160 | 53.827 | 1.07 |

Purity

| No.<br>UV_VIS_1 | Time<br>UV_VIS_1<br>min | Area<br>UV_VIS_1<br>mAU*min | Height<br>UV_VIS_1<br>mAU | Rel.Area<br>UV_VIS_1<br>% | |
|---|---|---|---|---|---|
| 1 | 7.89 | 0.867 | 11.350 | 0.72 | |
| 2 | 8.02 | 1.880 | 24.639 | 1.57 | |
| 3 | 8.22 | 1.750 | 20.925 | 1.46 | |
| 4 | 8.35 | 7.658 | 101.635 | 6.40 | |
| 5 | 8.47 | 98.416 | 917.988 | 82.24 | product |
| 6 | 8.74 | 2.072 | 6.075 | 1.73 | |
| 7 | 8.87 | 1.502 | 16.115 | 1.26 | |
| 8 | 9.05 | 3.013 | 27.360 | 2.52 | |
| 9 | 9.32 | 0.325 | 4.005 | 0.27 | |
| 10 | 10.97 | 0.618 | 6.586 | 0.52 | |
| 11 | 11.64 | 1.566 | 12.860 | 1.31 | |

Purity

| No.<br>UV_VIS_1 | Time<br>UV_VIS_1<br>min | Area<br>UV_VIS_1<br>mAU*min | Height<br>UV_VIS_1<br>mAU | Rel.Area<br>UV_VIS_1<br>% |
|---|---|---|---|---|
| 1 | 8.32 | 1.291 | 19.623 | 0.32 |
| 2 | 8.59 | 40.959 | 351.465 | 10.10 |
| 3 | 8.95 | 321.649 | 1738.204 | 79.31 |
| 4 | 9.40 | 4.934 | 41.297 | 1.22 |
| 5 | 9.70 | 24.522 | 143.348 | 6.05 |
| 6 | 10.22 | 2.542 | 18.029 | 0.63 |
| 7 | 12.45 | 9.655 | 55.952 | 2.38 |

PROCESS FOR SOLID-PHASE PEPTIDE SYNTHESIS AND DEVICE

The ASCII text file "SequenceListingETL.txt" created on Jan. 14, 2026, having the size of 936 bytes, is incorporated by reference into the specification.

BACKGROUND OF THE INVENTION

Field of the Invention

The invention relates to a method for carrying out solid-phase peptide synthesis, to an automated parallel solid-phase peptide synthesis, and to a device adapted to carry out such a method.

Background Art

Solid-phase peptide synthesis (SPPS or also Merrifield synthesis) is a peptide synthesis method introduced in 1962 by Nobel prize winner Robert Bruce Merrifield in which an insoluble polymeric support is used. A linear peptide is constructed by stepwise attachment of the sequence-specific, temporarily protected amino acids, with the C-terminal end of the growing polypeptide chain being covalently linked to a synthetic resin support. To ensure a controlled reaction and to avoid side reactions, reactive functional side chains of the amino acids must be blocked by suitable protecting groups. While the α-amino group of the amino acid to be linked only needs to be protected during the actual coupling reaction, permanent side-chain protecting groups are only split off from the peptide after the synthesis has been completed. In contrast to ribosomal protein biosynthesis, the extension of the peptide chain occurs from the C- to the N-terminus. A copolymer of polystyrene and 1-2% 1,4-divinylbenzene has proven to be a suitable polymeric support. The resin beads obtained by bead polymerisation with a diameter between 20 and 100 μm swell in the solvents used for the synthesis and thus become permeable to the reagents. The tert-butyloxy-carbonyl (Boc) and fluorenyl-9-methoxycarbonyl (Fmoc) groups are mainly used as intermediate α-amino protecting groups. The Boc group is stable with respect to catalytic hydrogenation and alkaline hydrolysis and can be split off by mild acidolysis, e.g. with 50% trifluoroacetic acid (TFA). The constant repetition of acid deblocking reactions after the individual coupling steps can lead to partial deblocking of side-chain protecting groups as well as to minor hydrolysis of the anchor bond to the polymeric support. The Fmoc group has the advantage that it can be split off by treatment with suitable bases, such as morpholine, 2-aminoethanol or piperidine. If acid-labile, base-resistant groupings are used as anchor groupings on the polymeric support and in order to protect the third functions of corresponding amino acid building blocks, intermediate and permanent protecting groups can advantageously be split off independently of each other.

The coupling reaction (also referred to as condensation or peptide propagation) is an extremely important step for the synthesis, because a complete conversion is the basic requirement for the uniformity of the final product. As a rule, the reagent is used in excess, with preference being given to anhydrides, active esters or so-called in-situ activators, in which intermediately activated ester derivatives are formed. The constantly repeating reaction steps of splitting off the α-amino-protecting group and attachment of the next Na-protected amino acid (coupling reaction, condensation) have enabled the extensive automation of the synthesis steps and construction of peptide synthesisers, most of which work according to the flow-through principle. The resin is placed here in a column with a frit at the bottom so that reagents and solvents can be automatically fed in, mixed with the support material, and then extracted. The steps are repeated until the desired length of peptide to be constructed is reached. Lastly, the synthesised peptide is detached from the polymeric support. Detachment from the resin matrix is achieved by means of reagents which, depending on the protecting group scheme chosen, selectively split off the anchor bond between the C-terminal amino acid and the support, or synchronously cause partial or complete deblocking of the synthesised peptide. Multiple peptide synthesis was developed from solid-phase peptide synthesis. [E. Atherton and R. C. Sheppard Solid-Phase Synthesis-A Practical Approach, Oxford University Press, 1989; H.-D. Jakubke Peptides: Chemistry and Biology, published by Spektrum Akademischer Verlag Heidelberg, 1996]

A major challenge of automated peptide synthesis is to avoid cross-contamination, since in known procedures and automated installations the reagents are passed through the same tubing systems and cannulas. To prevent cross-contamination, in known equipment arrangements the entire system is rinsed with large volumes of rinsing agents.

DE 101 31 088 B4 starts here and provides a device that enables automated, simultaneous, multiple and parallel synthesis in which cross-contaminations can be excluded. This leads to a significant reduction in synthesis time.

Another approach to reduce the synthesis time in peptide synthesis is to expose the reagents to microwave radiation during synthesis. This makes it possible to reduce the synthesis time to one tenth. However, microwave-assisted reactions have to be carried out in special protected spaces. The method is therefore limited to smaller reactors and thus low throughput quantities. In addition, it has been found that not all of the usual protecting groups are stable with respect to microwave radiation, so that reduced yields and more impurities may occur.

In 1977, an attempt to assist the synthesis by means of ultrasound was published in CA 101 93 24. However, it became apparent in the following years that this method, at least in the form shown, did not lead to the desired results. No reproducible acceleration of the synthesis time could be observed with the usual methods.

SUMMARY OF THE INVENTION

It is now the object of the invention to further accelerate the synthesis time of a solid-phase peptide synthesis while maintaining or improving the yield and purity. The method is to be applicable in particular to automated, parallel methods.

This object is achieved by a method for carrying out an automated parallel solid-phase peptide synthesis and also by a device for carrying out said method having the features of the independent claims.

Therefore, a first aspect of the invention relates to a method for carrying out solid-phase peptide synthesis (hereinafter also referred to as synthesis or peptide synthesis). The method according to the invention comprises the steps of a) binding an amino acid protected at the N-terminus by a protecting group to a solid support material via a C-terminus of the amino acid, b) splitting off the protecting group, c) performing at least one peptide propagation, and d) terminating the reaction by splitting off the peptide from the support material, wherein steps a) to d) take place in a liquid reaction medium and, at least during one of the steps, ultrasound with a frequency in the range of >25 to 2000 kHz acts at least intermittently on the reaction medium.

It has been found that ultrasound only has an accelerating effect on the reactions in question in solid-phase peptide synthesis from a frequency of more than 40 kHz. The method according to the invention thus enables a reproducible reduction of the synthesis time in solid-phase peptide synthesis so as to be at least in the region of the synthesis time in microwave-assisted peptide synthesis. Advantageously, however, no special safety precautions have to be taken. Furthermore, the necessary equipment is less expensive to procure and maintain. This means that the method can be used for almost any synthesis set-ups, and especially for parallel and/or automatable synthesis set-ups.

Step a) is understood here to mean that a functional group is bonded directly or indirectly to a suitable support material, for example a preloaded or non-preloaded resin or an amide resin for solid-phase peptide synthesis. This functional group may in particular be protected by means of an Fmoc protecting group. Here, preloaded or non-preloaded refers to the fact that at least one first and optionally at least one following amino acid, i.e. the primary amino acids in the amino acid sequence to be synthesised, is already directly bonded to the support material.

Frequencies of more than 40 kHz, preferably more than 50 kHz, in particular more than 75 kHz, particularly preferably more than 100 kHz, have proven to be particularly suitable, as a more significant synthesis time reduction can be achieved with higher frequency. It has been found that the formation of cavities is significant for the positive effect on peptide synthesis, especially the increase in quality. The associated cavitation starts from a frequency of 40 KHz and intensifies with increasing frequency. In the frequency range from 20 to 40 kHz, only vibrational excitations take place.

Preferably, the ultrasonic frequencies of the method according to the invention do not exceed 2 MHz, in particular 1 MHz. Further explanations of preferred frequencies follow.

The ultrasound-assisted solid-phase peptide synthesis (USPS) described here belongs to the category of sonochemistry in chemical synthesis.

The chemical effect of ultrasound cannot be a direct effect of the sound field, as the usual frequencies are several orders of magnitude too low to excite even a simple rotational movement.

It is assumed that the positive effect is directly related to the cavitation triggered by ultrasound and the pressure pulses generated as a result. Cavitations occur in a frequency range from 40 kHz to 2 MHz.

Three types of sonochemical reactions are postulated.

1. In homogeneous systems by radical or radical-ionic intermediates. In the cavitation bubble, extreme pressure and high temperatures produce, for example, $OH^-$ and $H^-$ radicals in the aqueous phase, which cause, among other things, the formation of $H_2O_2$ in the bubble.

2. In heterogeneous systems by ionic reactions. These are mainly assisted by the mechanical effects of cavitation in the solvent. Asymmetric bubbles form on solid particles. The bursting of the asymmetric bubbles on the particles creates liquid jets that shoot towards the unilaterally bursting bubble. This assists the absorption of solvents and dissolved substances into the porous material. At other liquid phases, on the other hand, mixing of the phases takes place.

3. In heterogeneous systems, where radical reactions can also take place. It may be that the radical pathway produces different products as compared to the ionic pathway, such as in the Kornblum-Russell reaction.

Cavitation bubbles are more likely to form in lower frequency ranges, which then also become larger and asymmetrical. This results in a stronger but more uneven mixing. At higher frequencies, on the other hand, a greater number of smaller, symmetrical bubbles are created and there is more radical exchange between the cavitation bubbles and the environment.

Cavitation is "the formation, growth and implosive collapse of bubbles in a liquid. Cavitation collapse causes locally high temperatures (~5000 K), high pressures (~1000 atm), enormous heating and cooling velocities (>109 K/sec)" and liquid jets (~400 km/h). Cavitation bubbles are vacuum bubbles (Suslick 1998). The vacuum is created by a fast-moving surface and an inert liquid. The resulting pressure differences overcome the cohesive and adhesive forces within the liquid.

From a frequency of 110 KHz and more, in particular from 125 kHz, preferably at 130 kHz and more, an accelerated reaction process and the associated shortened reaction time as well as an improvement in the yield can be observed. It has been found that, compared to standard systems, it is not necessary to work with a 40-fold excess of amino acid, but the same results can already be achieved with a 4-fold excess. This in turn leads to significantly reduced quantities of reactants and thus to considerable cost savings. In addition, no racemisation was observed at frequencies in the range of 110 to 500 kHz, which leads to high yields.

In a preferred embodiment of the method according to the invention, it is provided that the ultrasound is transmitted to the reaction medium via an external liquid bath. This is a clear difference to means which transmit the ultrasound directly or exclusively via solid transmission means to the reaction medium. It has been found that transmission via at least one liquid medium provides more consistent, reproducible and gentle synthesis results. The necessary synthesis time showed a lower dispersion when using a transmission medium comprising a liquid than, for example, the synthesis time using a probe immersed in the reaction medium. In addition, the test set-up is much simpler than when using a probe. Immersion of a probe would inevitably lead to contamination of the probe and require regular cleaning of the probe, which would equal or at least significantly reduce the gain in synthesis time.

The amount of energy that is converted into cavitation depends on several factors that indicate the motion that is transferred from the cavitation-generating equipment to the liquid. The intensity of the acceleration is one of the most important factors affecting the efficient conversion of energy into cavitation. Higher acceleration produces higher pressure differences. This increases the likelihood of creating vacuum bubbles instead of waves in the liquid. This means that the higher the acceleration, the higher the proportion of energy that is converted into cavitation. In the case of an (ultra) sonic transducer, the intensity of the acceleration is determined by the amplitude of the vibration. In addition to the intensity of the ultrasound, it is also important that the liquid is accelerated in such a way that the losses from turbulence, friction and wave generation are as low as possible. The path of the unilateral direction of movement is best suited for this.

Therefore, the choice of the transmission medium is crucial for the effect in peptide synthesis. In addition to the choice of state, the substance of the transmission medium must also be optimised. In addition to water as the transmission medium, organic solvents, in particular lower and medium alcohols, such as ethanol, propanol and butanol, are also preferably used as the transmission medium.

It is advantageous to select different transmission media in combination. The test set-up is to be understood as a bath-in-bath. In other words, the reaction takes place in a reaction medium which is arranged in a (reaction) vessel. This reaction vessel is in turn arranged in a vessel with a first transmission medium, which in turn is arranged in a further transmission medium. The ultrasound is thus transmitted via the further transmission medium to the first transmission medium and from there to the reaction medium.

With particular advantage, the first transmission medium is constituted by low and medium alcohols, in particular of the aforementioned type and/or the further transmission medium is constituted by water.

With high ultrasonic frequencies, the temperature in the liquid bath increases as expected. At frequencies up to 500 KHz, however, this effect can be controlled very well, since the temperature increase that occurs can easily be compensated for with a cooling device, such as the cooling of the water bath by means of a continuous cooler (cryostat) or Peltier elements, so that the racemisation that potentially also occurs here does not impair the yield.

When using frequencies significantly above 500 kHz up to 1000 KHz or higher, it became apparent that for quality assurance purposes it makes sense to counteract the temperature increase, for example by cooling the bath.

The ultrasonic bath is preferably subjected to temperature control, more specifically to a temperature range from 20 to 100° C., preferably from 20 to 70° C., particularly preferably from 40 to 50° C.

In a further preferred embodiment of the invention, it is provided that the amino acid is protected at the N-terminus by a base-labile, in particular a temporary (primary) protecting group that can be split off by means of secondary amines, in particular fluorenylmethoxycarbonyl (Fmoc). Compared to the protecting groups used in boc methods, these protecting groups proved to be particularly stable to ultrasound at the frequencies according to the invention, so that particularly high yields with high purity could be achieved. Deprotection is preferably carried out using a suitable base, as described above or in the test results. Preferably, 20% piperidine in DMF (dimethylformamide) is used.

So far, the advantage of ultrasound-assisted peptide synthesis has only been confirmed for BocOC synthesis. It has even been found that ultrasound assistance is not indicated for Fmoc-based synthesis because the resins used pulverise under ultrasound. Due to the different reaction media and protecting groups of the side chains used, it has been assumed that only the coupling to the resin can be assisted by ultrasound. Surprisingly, however, an advantage in terms of reaction time and yield could also be shown for Fmoc-based peptide syntheses by ultrasound assistance during the individual synthesis steps with the present method in the frequency ranges described.

Reactive side chains of the peptides to be synthesised by means of the method according to the invention are preferably also protected by (secondary) protecting groups. Depending on the functional groups to be protected, acid-stable protecting groups, in particular to be selected from the group consisting of S-2,4,6-trimethoxybenzyl (Tmob), triphenylmethyl (Trt), tert-butyl (tBu), tert-butyloxycarbonyl (Boc), 2,2,4,6,7-pentamethyldihydrobenzofuran-5-sulfonyl (Pbf), have proven to be particularly stable in the peptide synthesis according to the invention by means of ultrasound in the frequency range mentioned.

With reference to the method according to the invention, for example, Fmoc amino acids selected from the following group, in which the amino acid is listed as a single-letter code or three-letter code, are particularly suitable for peptide propagation: Fmoc-A-OH, Fmoc-C(Trt)-OH, Fmoc-D (OtBu)-OH, Fmoc-E (OtBu)-OH, Fmoc-F-OH, Fmoc-G-OH, Fmoc-H (Trt)-OH, Fmoc-I-OH, Fmoc-K(Boc)-OH, Fmoc-L-OH, Fmoc-M-OH, F moc-N(Trt)-OH, Fmoc-P-OH, Fmoc-Q-Trt-OH, Fmoc-R-Pbf-OH, Fmoc-S-tBu-OH, Fmoc-T-tBu-OH, Fmoc-V-OH, Fmoc-W (Boc)-OH, Fmoc-Y-(tBu)-OH, Fmoc-Gln (Tmob)-OH, Fmoc-Asn(Tmob)-OH. This refers to both the L-forms and the D-forms of the amino acids.

In addition, special side-chain-protected post-translationally modified amino acids can also be used, such as:

for the phosphorylation of Ser/Thr:

Fmoc-Ser(PO(OBzl)OH), Fmoc-Thr(PO(OBzl)OH), Fmoc-Tyr(PO(OMe)$_2$), Fmoc-Tyr(PO(OBzl)OH), Fmoc-Tyr(PO(OBzl)$_2$)-OH, Fmoc-Tyr(PO$_3$H$_2$)—OH, Fmoc-Tyr(PO(NMe$_2$)$_2$), Fmoc-Tyr(PO(NMe$_2$)$_2$), Fmoc-Ppa(Bzl)-OH, Fmoc-Pmp-OH, Fmoc-F2Pmp-OH, for the sulphation of Tyr:

Fmoc-Tyr(SO$_3$nP)-OH, Fmoc-Tyr(SO$_3$DCV)-OH, for the methylation of Arg:

Fmoc-Arg(Me,Pbf)-OH, Fmoc-ADMA(Pbf)-OH, Fmoc-SDMA(Boc$_2$)-ONa, for the methylation of Lys:

Fmoc-Lys(Me, Boc)-OH, Fmoc-Lys(Me$_2$)—OH, Fmoc-Lys(Me$_3$Cl)—OH for citrullination:

Fmoc-citrulline-OH for the glycosylation of Asn:

Fmoc-Asn(β-DGIcNAc(Ac)$_3$)-OH, Fmoc-Asn(β-DG-IcNAc(Ac)$_3$-(1-4)-β-DGIcNAc(Ac)$_2$)-OH for the glycosylation of Ser/Thr:

Fmoc-Ser/Thr(α-DGInNAc(Ac)$_3$)-OH, Fmoc-Ser/Thr(β-DGal(Ac)$_4$-(1-3) α-DGInNAc(Ac)$_2$)-OH, Fmoc-Ser/Thr(sialylOMe(Ac)$_4$-(1-6)-α-D-GlnNAc(Ac)$_2$)-OH, Fmoc-Ser/Thr(sialylOMe(Ac)$_4$-(1-3)-β-D-Gal(Ac)$_3$-(1-3) α-DGInNAc(Ac)$_2$)-OH.

Likewise, synthetic building blocks developed for the synthesis of complex peptide sequences can be used, such as FmocPseudoProline dipeptides, so-called Dmb building blocks: such as Fmoc-(Dmb)Gly-OH, or as dipeptide FmocXaaDmbGly, Hmb building blocks: FmocHmbXaa, as well as Hmsb building blocks, Hnb building blocks, Mmsb building blocks, non-natural amino acids such as:

naphthylalanines, Fmoc-L-2Nal-OH ornithines, Fmoc-L-Orn(Aloc)-OH as well as the methylated variants polyethylene glycols, Fmoc-O1Pen-OH, Fmoc-AEEP, Fmoc-TTDS-OH and all other Fmoc-protected amino polyethylene glycol acids.

Particularly derivatised amino acids such as:

Fmoc-Lys(biotin)-OH, FMOC-Lys(Cy5)-OH.

In general, all building blocks can be used in the USPS that have a temporarily protected amine function, preferably Fmoc-protected, and a carboxylic acid function that can be converted into an active ester or an amine-reactive group.

Advantageously, ultrasound acts on the reaction medium in exactly one step, in particular in step c). Alternatively or additionally, ultrasound acts on the reaction medium in at least one further step, preferably step a), b) and/or step d).

The reaction-accelerating properties of the ultrasound according to the invention can be observed in each of the steps mentioned.

Here it is particularly preferred that the action of the ultrasound is not interrupted between or in the individual steps, as an interruption can lead to reduced yield.

The greatest reduction in synthesis time with high yields, until now, was achieved when ultrasound was applied to the reaction medium during the entire synthesis, i.e. also during washing, deprotection, condensation and coupling. In contrast, ultrasound is not necessarily advantageous during the pre-swelling as a preparatory step, nor during the final washing.

Solid-phase peptide synthesis comprises several washing steps that can be distinguished from one another. The individual types of washing steps can be distinguished by their respective upstream reactions. Thus, at least one washing after the coupling of the first amino acid to the resin (initial washing), a washing after step b), the decoupling of the protecting group (hereinafter step $W_b$), a washing after the coupling of an amino acid for the extension of the peptide chain (hereinafter step $W_c$), and a final washing after step d), the splitting off of the last temporary protecting group of the finished peptide from the support material (hereinafter step $W_a$), can be mentioned.

During the individual washing steps, ultrasound also preferably has an effect on the reaction and causes a significant reduction in the necessary rinsing agent and rinsing time. Thus, washing with only one rinsing step with ultrasound already achieves the same results as rinsing usually four times in standard synthesis. The washing step $W_c$, i.e. washing after step c), is particularly important for increasing yield and quality. Investigations have shown that the washing step $W_b$ can even be dispensed with completely. Preferably, however, all washing steps are carried out in the method according to the invention.

Preferred, in particular for this washing step, are ultrasonic frequencies in the range of 100 to 500 kHz, preferably in the range of 100 to 200 KHz, in particular in the range of 120 to 140 KHz. In these ranges, the amount of solvent necessary for washing or rinsing, for example DMF, both within the individual rinsing cycles of a washing step, could be reduced in such a way that only one single rinsing step per washing step $W_b$ is necessary.

With particular advantage, it is provided that ultrasound acts on the reaction medium in the above-mentioned frequency ranges during all steps of the peptide synthesis a) to d) including the washing steps $W_b$, $W_c$ and $W_a$, in particular without complete interruption.

It was found that, depending on the peptide to be synthesised, different frequencies are optimal for the individual steps a) to d) and in particular for steps $W_{b, c\ and\ d}$ with regard to increasing quality and reducing reaction time, i.e. they show more beneficial effects. Thus, it is preferred that ultrasound acts on the reaction medium at different frequencies in the individual steps. In particular, it is preferred that the frequency changes between the steps and/or that ultrasounds with different frequencies are superimposed on each other.

The support material is a material that is known fundamentally to the person skilled in the art for peptide syntheses. These are artificial resins/synthetic resins, with resins from the following group being particularly advantageous:

Knorr Amid Resin LS 1% DVB, Wang Resin, Chlorotrityl Resin, PRG Resins, Tentagel Resins, Chemmatrix Resins.

Generally preloaded or non-preloaded and/or functionalised resins for solid phase synthesis.

Synthetic resins that are not paramagnetic are preferred, since the separation of the synthesised peptides by means of magnetism is significantly more complex than by means of filtration and it has been shown that paramagnetic resins are crushed in ultrasound at low frequencies (up to 40 kHz) up to the formation of very fine particles and in the course of this process clog the filter materials.

In the context of the invention, preferably used solvents are DMF (N,N-dimethylformamide), NMP (N-methyl-2-pyrrolidone) or DMA (N,N-dimethylacetamide).

The base used to catalyse the condensation reaction is preferably NMP, 4-methylmorpholine or DIPEA, diisopropylethylamine in DMF or another solvent.

A solution for splitting off the temporary Fmoc protecting group is preferably 20% piperidine in DMF. Other splitting-off methods are known in principle to the person skilled in the art.

Preferably, the coupling reagent used is HBTU (2-(1H-benzotriazol-1-yl)-1,1,3,3-tetramethyluronium hexafluorophosphate), HCTU (2-(6-chloro-1H-benzotriazol-1-yl)-1,1,3,3-tetramethylaminium hexafluorophosphate), PyBOP (benzotriazol-1-yl-oxytripyrrolidinophosphonium hexafluorophosphate), DCC, dicyclohexylcarbodiimide; DIC, diisopropylcarbodiimide; or EDC, 1-ethyl-3-(3-dimethylaminopropyl) carbodiimide.

All amino acids/reagents are dissolved in the solvent used, thereby obtaining the reaction medium/reactant medium/reagent solution. When reagents are referred to in the context of the method and device, this is also understood to include a solution of the reagents.

The concentration of the amino acid used always depends on the synthesis scale and its solubility in the solvent used, such as DMF, NMP or DMA.

In order to obtain a good synthesis result, the amino acids to be coupled (AA) and the reagent for the formation of the active ester (activator) are preferably each used at least equimolar to the synthesis scale. However, it is usual to use the AA and the activator together in equimolar amounts and to use them both in excess to the synthesis scale.

Excesses range from 4-fold to 100-fold. To achieve qualities comparable to the method of the invention with prior art solid-phase peptide synthesis, at least a 40-fold excess is required, depending on the peptide sequence. The reason is that the high excess of the reactants favours the formation of the product, namely the extended peptide chain. The concentration of the amino acid here primarily depends on the solubility of the protected AA in the solvent used and is preferably between 0.2M-0.6M.

In the experiments described in this application, the amino acids were used at a concentration of 0.4M.

Again, it is advantageous that the ultrasound is never completely interrupted between successive (ultrasound-assisted) steps a)-d), but only the frequency is changed. Advantageously, it is envisaged that the method is carried out semi-automated/automated and/or in parallel. In a combination of parallel automated methods with the ultrasound assistance according to the invention, it is possible to produce individual peptides, i.e. peptides tailored to a specific individual, on a scale and with a throughput that makes the particular form of cancer therapy with neoantigens accessible to a large number of patients. Neoantigens are mutation-induced changes in proteins of tumour cells. They can be identified with the technique of Next-Generation Sequencing (NGS). Usually, the number of different neoantigens ranges between 100 and 200. A corresponding number of synthetic peptides can mimic these neoantigens in vitro and be used for tumour-specific immunisation of a patient. The number, composition and amino acid sequences of the neoantigens are individual for each patient. Thus, the replication of the corresponding peptides must also be adapted from individual to individual, in other words personalised. In order to make this promising therapy medically usable at all, it must be possible to conduct studies on a large number of patients under the same conditions within a reasonable period of time. This requires that a large number of personalised antigens can be made available in an extremely short time. The described form of personalised cancer therapy thus places high demands on speed, parallelism and quality for the synthesis of peptides. The method according to the invention can meet these requirements.

The method according to the invention is particularly suitable for large-scale application. The term "large-scale application" means scales of 1 l to 50 l, in particular 100 to 500 l batch size.

Thus, a further aspect of the invention is an automated parallel solid-phase peptide synthesis comprising the method according to the invention in one of the described embodiments.

The method according to the invention is carried out with particular advantage at room temperature or at a moderate temperature increase. Reaction temperatures in the range from 20 to 100° C. are particularly preferred, preferably in the range from 20 to 70° C., in particular in the range from 40 to 60° C. The temperature control preferably takes place at least in step a), b) and/or d).

It has been found that the method according to the invention is, among other things, particularly suitable for the large-scale production of litraglutide and semaglutide, in particular on a scale of more than 100 g of product.

A further aspect of the invention relates to a device for carrying out a solid-phase peptide synthesis, which device is designed to carry out the method according to the invention in one of the embodiments described. For this purpose, the device according to the invention comprises an ultrasonic transducer which preferably transmits ultrasound of a frequency of 25 KHz to 2 MHz, in particular in the-range of 40 kHz to 1 MHz, preferably in the range of 100 to 500 kHz, to the reaction medium via a liquid transmission medium.

The device preferably has a means for receiving one or more synthesis vessels with at least one opening for filling in reactant media, in particular a synthesis plate in microtiter plate format with 96, 384, 1536 or 3456 reaction chambers, a synthesis cylinder or a synthesis flask or synthesis reactor, and an ultrasonic bath comprising a transmission liquid, wherein the synthesis vessel can be arranged in the ultrasonic bath in such a way that the synthesis vessel is wetted to a minimum height with the transmission liquid of the ultrasonic bath.

Advantageously, minimum height is understood to mean a height that ensures transmission of the ultrasound from an ultrasonic transducer of the ultrasonic device to the reaction medium in such a way that the sound occurs almost exclusively via the liquid transmission medium. For this purpose, the height of the surface of the transmission medium on an outer surface of the synthesis vessel corresponds to at least half a height, preferably a height in the range from half to full height, preferably three quarters to full height, of a meniscus of the reaction medium in the synthesis vessel.

The synthesis vessel is preferably designed as a synthesis plate, for example as a microtiter plate, in particular parallel and juxtaposed synthesis cylinders, for example in the form of beakers or syringes, or as a synthesis flask, for example a round-bottomed flask or a reactor (for example according to Höchst or Syringe). In particular, the design of the synthesis vessel as a round-bottomed flask or reactor is preferred for use in large-scale semi-automated/automated solid-phase peptide synthesis, since scales of 1-50 l in the flask or 100 to 500 l in the reactor can be handled.

The use of microtiter plates or parallel synthesis cylinders, on the other hand, is particularly preferred for parallel and automated solid-phase peptide synthesis, whereas the aforementioned are more commonly used for large-scale application of individual peptides such as litraglutide and semaglutide. The invention proposes a device that operates entirely without dilutors and tubing systems for the supply and metered delivery of the synthesis building blocks. Separate synthesis pens are provided for the individual synthesis building blocks and are provided in a holder of the synthesis device for the synthesis and are gripped and picked up from this holder by the gripper arm of the device in order to deliver a metered quantity of the building block onto the support material located in a reaction chamber of a synthesis vessel, in particular a synthesis plate.

Reagent reservoir and dosing device thus form a self-contained unit. This eliminates all rinsing processes and the associated disadvantages that were previously necessary when changing the synthesis building blocks and reagent distribution.

An area is defined for parallel synthesis (FIG. 2). The working region is dimensioned in such a way that every point of the working region can be reached by the synthesis pen moved by the gripper arm. Preferably, up to 10 synthesis stations are arranged on this working region, in particular symmetrically. The dimensions of the synthesis station are preferably based on standard microtiter plates. A synthesis station can be of modular design and can comprise a base part with a connection for the extraction of solvents and an exposed frame for holding the synthesis plate. Depending on the subdivision of the synthesis plates used, for example, 6, 12, 24, 48, 96, 384, 1536 or 3456 individual syntheses can be performed in parallel in one synthesis plate. For larger synthesis scales, synthesis cylinders or syringe bodies can be used in special receptacles.

According to the further features of the invention, the reaction chambers of the synthesis plates are closed on the opening side with a permeable material, for example with a frit. Sample plates for receiving the peptides dissolved after the splitting-off reaction can be arranged below the frame. With the proposed device for solid-phase synthesis, both the synthesis and the splitting off of the obtained compounds from the support material, the synthesis resin, are possible without manual intervention.

The sample plates are equipped with individual holding chambers which correspond in their arrangement and design to the grid of the reaction chambers in the synthesis plate. In this way, an error-free and easy assignment of the particular compound after its splitting-off from the support material or synthesis resin is ensured. A direct transfer of the reaction products to high-throughput screening lines is thus easily possible.

The synthesis pen (FIG. 3 and FIG. 4) has a hollow-cylindrical main body (reagent reservoir) which can be closed by a screw closure and a mouthpiece at the foot end which is adapted to the free opening of the reaction chambers in the synthesis plate and is equipped with an outlet opening. The outlet opening is closed by a valve needle with a stop valve, which are guided by a piston rod and a piston in the main body and are releasably fixed in their closed position by a compression spring acting on the piston. The cylinder space below the piston is used to hold a single synthesis building block and an inert gas, with the metered delivery of the reagent being effected by simply placing the mouthpiece on the permeable material with which the opening side of the reaction chamber is covered. At the same time, the stop valve is released from the valve seat by pressing in the valve needle, and the outlet opening is released. The amount of reagent dispensed is determined by the length of time for which the mouthpiece is placed on the permeable material. When the mouthpiece is lifted off, the outlet opening is automatically closed again.

In a further design of the synthesis pen (FIG. 6), the screw closure of the reagent reservoir is replaced by a movable lid with a bayonet closure. A piston rod, which is preferably arranged centered in the lid, in particular pressed in, leads through the entire synthesis pen into a dosing cylinder. The dosing cylinder is closed at the bottom, for example with a non-return valve. By pressing the lid, a defined amount of reagent is dispensed by means of a piston. A return means installed in the synthesis pen, for example a spring, returns the piston. At the same time or thereafter, the dosing cylinder is filled again. A suitable actuator in the foot-side mouthpiece, for example a non-return valve, ensures that solution can only be dispensed by active delivery. This design of the synthesis pen allows contact-free dispensing into the reaction chamber. The closed design of the synthesis pen with a closed reagent reservoir ensures high reagent stability.

Advantageously, the ultrasonic bath of the device according to the invention can be lowered or raised. This enables the reaction vessel to be lowered in the ultrasonic bath, preferably in several steps or continuously up to the predetermined height.

In addition, the ultrasonic bath can be used for different test set-ups, in particular different synthesis vessels.

The ultrasonic bath is also advantageously temperature-controllable, in particular designed to achieve a controlled temperature range of 20 to 100° C., preferably a range of 20 to 70° C., in particular a range of 40 to 60° C. In particular, the device has a cooling system for reducing the temperature of the bath, for example as a result of heating by high ultrasonic frequencies. This is particularly advantageous when using frequencies from 500 kHz, in particular from 1000 KHz.

Furthermore, the ultrasonic bath or its ultrasonic generator of the device according to the invention is designed to generate variable frequencies, in particular at least one in the low-frequency range (40-75 kHz) and one in the high-frequency range (100 to 2000 kHz, preferably 100 to 500 KHz) and to transmit them to the liquid bath. For this purpose, it is advantageous if the different frequencies can be switched on alternatively or additively to each other.

In a preferred embodiment, the ultrasonic bath, or rather the ultrasonic generator of the ultrasonic bath, is equipped with necessary powers in the range of 40 to 100 W, in particular in the range of 50 to 70 W nominal power, with peaks in the range of 100 to 300 W, preferably in the range of 170 to 280 W, for large-scale applications in the range of 250 to 700 W, in particular in the range of 500 to 600 W being achieved.

By using separate synthesis pens for each synthesis building block and covering the reaction chamber in the synthesis plates on the opening side, the risk of contamination is significantly reduced and cross-contaminations are virtually eliminated. Carry-over of synthesis building blocks, as often occurred with insufficient rinsing processes, is no longer possible.

With the elimination of the rinsing processes, not only is the consumption of organic solvents considerably reduced, but synthesis is also accelerated many times over.

The described embodiments can advantageously be combined with each other, unless otherwise described in an individual case. The embodiments of the invention otherwise apply equally to the method and the device.

In the following, the invention will be explained in greater detail with practical examples and results serving for illustrative purposes only. The accompanying drawings show:

DETAILED DESCRIPTION OF THE PREFERRED EMBODIMENT

Figure 1:
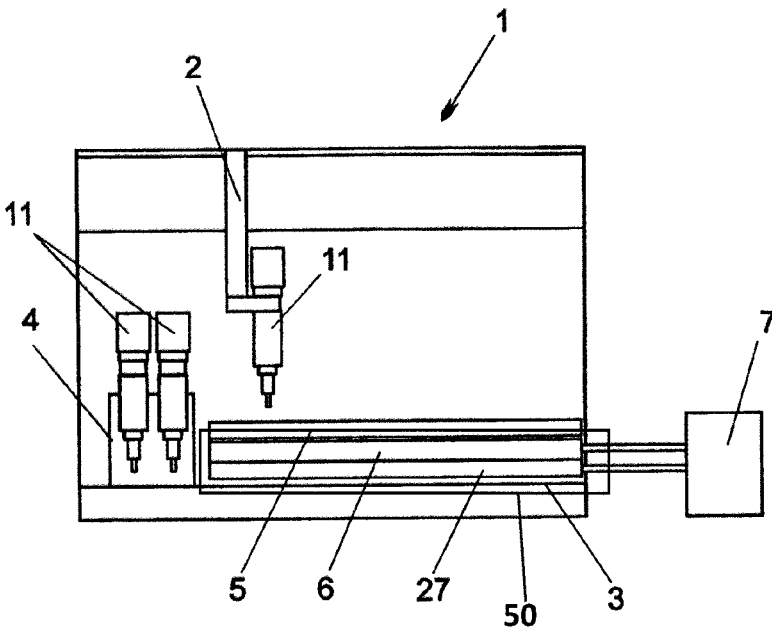
FIG. 1 a schematic representation of the device according to the invention for the synthesis of peptides, FIG. 2 the plan view of the working region of the device according to FIG. 1, FIG. 3 a schematic representation of the synthesis pen for separate feeding, dosing and reagent storage in a preferred embodiment of the invention, FIG. 4 a longitudinal section through the synthesis pen according to FIG. 3, FIG. 5 section A-A of FIG. 2 through a synthesis plate with the reaction chamber formed according to the invention, FIG. 6 a schematic representation of a longitudinal section of a synthesis pen in a further preferred embodiment of the invention, FIG. 7 a schematic representation of the sequence of a method for solid-phase peptide synthesis according to a preferred embodiment of the invention, FIG. 8 a graphical representation of the stability of tryptophan with the method according to the invention on the basis of the synthesis of endomorphin, FIG. 9 a graphical representation of the stability of an acyl carrier protein (ACP) with the method according to the invention, FIG. 10 a graphical representation of the stability of an acyl carrier protein (ACP) using a prior art comparison method, FIG. 11 a graphical representation of the comparison of the average synthesis quality of the ACP peptide taking into account the synthesis strategy, FIG. 12 a graphical representation of the quality of the syntheses according to FIG. 11, FIG. 13 a graphical representation of the testing of stock solutions on amino acids of different solution durations, FIG. 14 a graphical representation of the comparison of single and double coupling, FIG. 15 a graphical representation of the comparison of single and double coupling and also amino acid excess, and FIG. 16 a graphical representation of the comparison of the average synthesis quality of a peptide using different ultrasonic frequencies.
Figure 2:
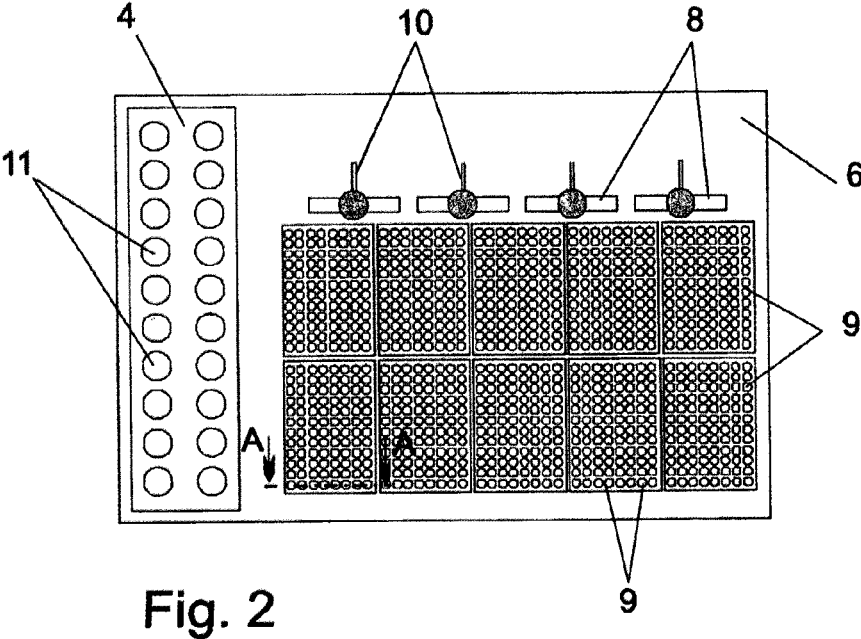
Figure 5:
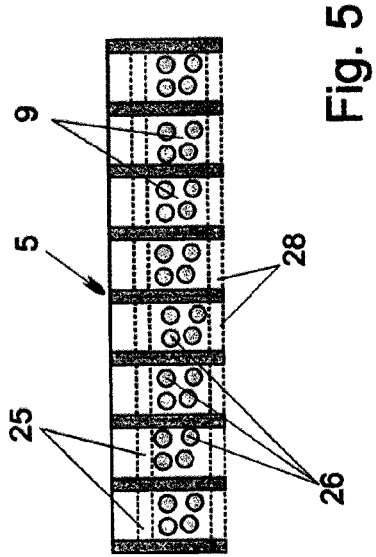
Figure 4:
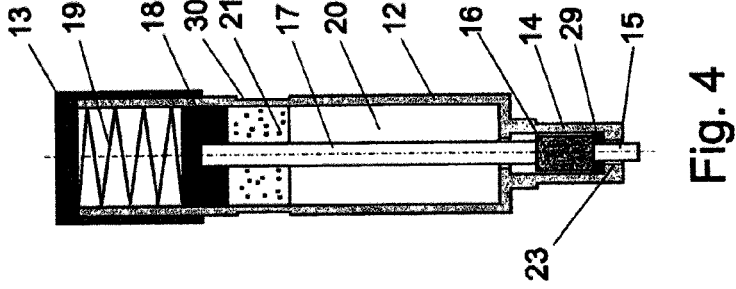
Figure 3:
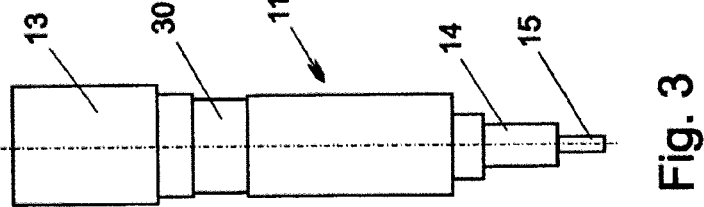

The synthesis device 1 shown schematically in FIG. 1 is based on a laboratory pipetting robot and has a gripper arm 2 that can be moved in the x, y and z axes. In the working region 3 there is a synthesis vessel, in particular synthesis plates 5, which with regard to the grid and the arrangement of the reaction chambers 9 are derived from microtiter plates known per se and have a 6, 12, 24, 48, 96, 384, 1536 or 3456 grid of the reaction chambers 9, whereby a high degree of parallelisation of the synthesis is achieved. The synthesis plates 5 are placed on a valve block 6 and have a membrane 28 of a porous material on the bottom side for sucking the used reagents and rinsing liquids out of the reaction chambers 9 into a waste by means of the valve block 6, which is connected to a suction pump.

The synthesis plate 5 is arranged together with the valve block 6 and the sample plate 27 in an ultrasonic bath 50, in particular one that is adjustable in height and can be switched on and off in a controllable manner. The ultrasonic bath 50 has a vessel with a liquid transmission medium in which the synthesis vessel 5 is arranged. Depending on the position of the ultrasonic bath 50, a meniscus of the synthesis vessel 5 of a reaction medium is at least up to half, preferably at least up to three quarters, in particular completely below a filling level of the transmission medium of the ultrasonic bath 5. The ultrasonic bath 50 is designed to transmit ultrasound with frequencies in the range of at least 25 kHz to 2 MHz via the transmission medium.

The synthesis device 1 is further equipped with one or more rinsing combs 8, which are connected to the corresponding rinsing agent reservoir via the rinsing agent supply lines 10. In order to rinse the samples located in the reaction chambers 9, to which a synthesis building block has been coupled, after the reaction time has elapsed and the spent reaction solution has been drawn off, the rinsing comb 8 with the required rinsing agent is picked up by the gripper arm 2 and moved over the reaction chambers 9 of the synthesis plates 5 for the metered delivery of the rinsing liquid. After rinsing, another rinsing comb 8 is used to supply the solution required for splitting off the temporary protecting group of the coupled synthesis building block, as described above. After an incubation time has elapsed, the splitting-off solution is drawn off via the valve block 6 with the aid of the suction pump 7 and the sample is washed. After washing, a new synthesis cycle starts, with which another synthesis building block is coupled.

According to the present invention, separate synthesis pens 11 are provided for each synthesis building block, in which pens the reagents 20 are placed in a closed space and can be coated with an inert gas 21. The individual synthesis pens 11 with the corresponding synthesis building block are provided in a holder 4 of the synthesis device 1 and brought to the reaction chamber 9 of the synthesis plates 5 by the gripper arm 2, which grips the synthesis pens 11 at the gripper arm holder 30, for metered delivery of the reagents.

The synthesis pen 11 used according to the invention consists of a hollow-cylindrical main body 12 with a mouthpiece 14 at the foot end and a screw closure 13 which tightly closes the cylinder space. In the mouthpiece 14 there is an outlet opening which is closed by a valve needle 15 and a stop valve 16 which, in the closed position, rests on a seal 29. The valve needle 15 and stop valve 16 are guided by a piston 18 via a piston rod 17. The required closing pressure for the stop valve 16 is generated by a compression spring 19, which rests on the piston 18 and is supported against the inner end face of the screw closure 13. The free space below the piston 18 is used for the presentation of the relevant synthesis building block 20, which is advantageously coated with an inert gas 21. In this way, highly reactive reagents can be kept stable over long periods of time under an inert gas atmosphere, which significantly improves the quality of the synthesis products.

In order to reliably exclude cross-contamination in the event of direct contact of the mouthpiece 14 with the sample, in accordance with the invention the reaction chambers 9, in which the samples or the solid phase 26, for example a synthetic resin, are located, are covered on the opening side with a permeable material 25, for example a frit. To couple a synthesis building block 20 to the sample or to the synthetic resin, the mouthpiece 14 of the synthesis pen 11 is placed on the permeable material 25 closing off the reaction chamber, whereby the valve needle 15 is displaced inwardly against the closing pressure of the compression spring 19 and the stop valve 16 is released. After this, the reagent solution can flow out freely, with the dosage of the solution flowing out being determined by the period of time for which the mouthpiece 14 is placed on the material 25.

With the splitting off of the last temporary protecting group and washing of the samples, the splitting off of the synthesis building blocks 20 coupled to the solid phase 26 takes place. For this purpose, a splitting-off solution is added to the samples by means of a rinsing comb 8 and a splitting-off reaction is initiated. After the incubation time has elapsed, the valve block 6 is switched in such a way that the compounds dissolved in the splitting-off solution are passed into the receiving chambers of a sample plate 27 which, according to a further feature of the invention, is arranged below the valve block 6 and is connected to an extraction system. The sample plates 27 correspond to the synthesis plates 5 with regard to their construction and design. With the transfer of the compounds dissolved from the solid phase 26 into the sample plate 27, the synthesis is completed.

Figure 6:
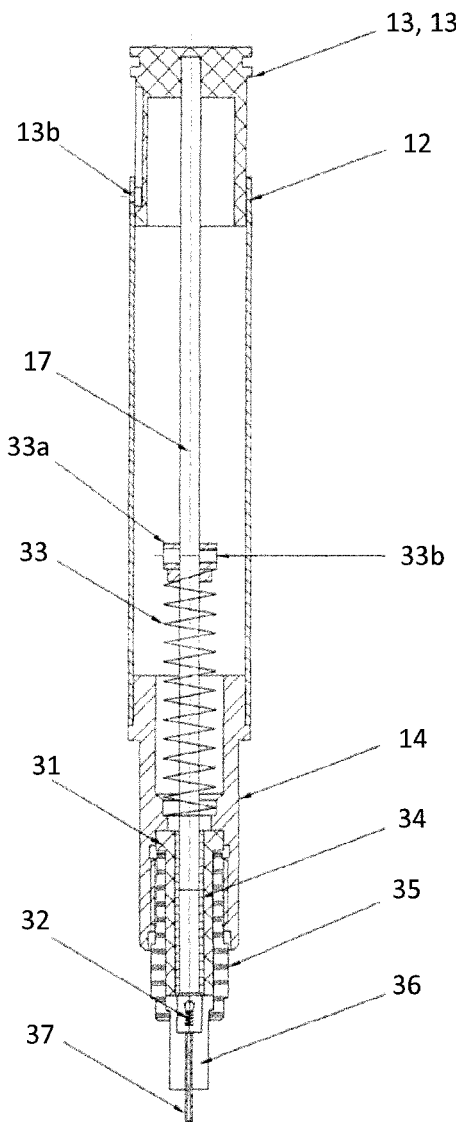

FIG. 6 shows a further preferred embodiment of the synthesis pen 11, where the same reference signs correspond to each other. The screw closure of the reagent reservoir is replaced in this design by a movable lid 13a with a bayonet closure. A piston rod 17, which is preferably arranged centered in the lid, in particular pressed in, leads through the entire synthesis pen into a dosing cylinder 31. The dosing cylinder 31 is closed downwards, for example with a non-return valve 32. By pressing the lid 13a, a defined quantity of reagent is dispensed by means of a piston. A return means installed in the synthesis pen 11, for example a spring 33, 33a, 33b, returns the piston. At the same time or downstream, the dosing cylinder is filled again 34. A suitable adjusting means in the foot-side mouthpiece 14, for example a non-return valve, ensures that solution can only be dosed by active delivery. This design of the synthesis pen 11 allows contact-free dispensing into the reaction chamber. The closed design of the synthesis pen 11 with a closed reagent reservoir ensures high reagent stability.

Figure 7:
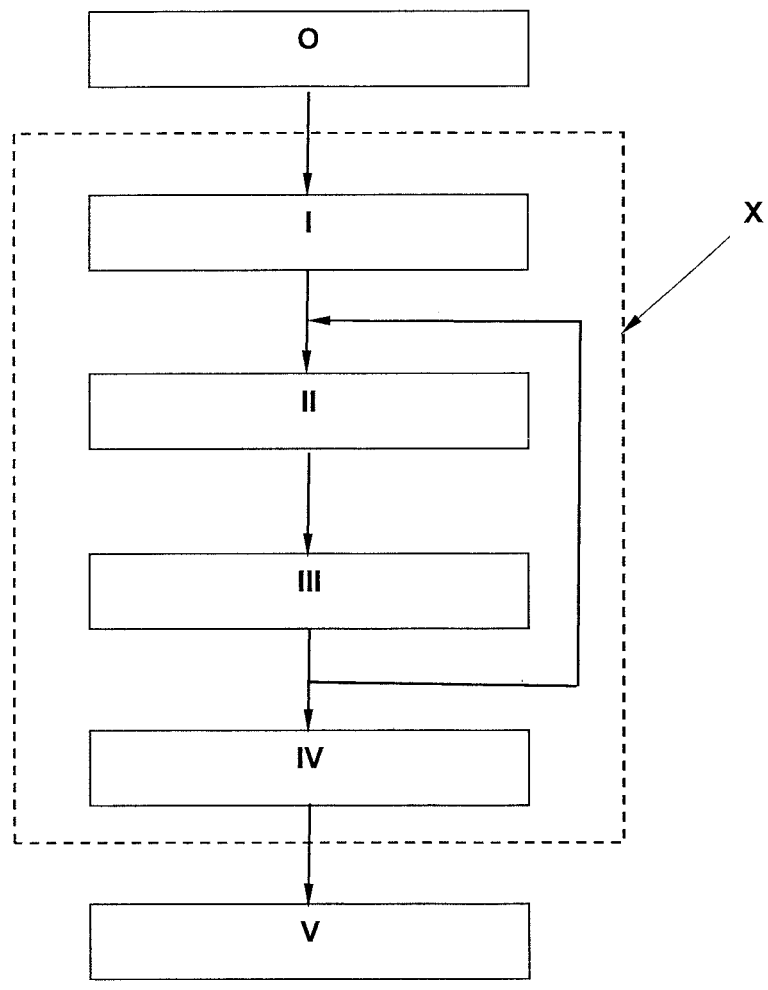

FIG. 7 shows a schematic representation of the method according to the invention.

The method according to the invention is part of a solid-phase peptide synthesis, as is or can be carried out by the device according to the invention. For this purpose, the N-terminus of an amino acid is protected from undesired reactions by a protecting group. The amino acid protected in this way is bound to a solid support material via its C-terminus (I). Subsequently, the N-terminus is deprotected (II) in order to bind another amino acid protected at the N-terminus to the N-terminus of the previous amino acid by means of peptide propagation (III). Steps II to III are repeated until the desired chain length of amino acids is reached. When the chain length is reached, the reaction is terminated in a step IV by splitting off the peptide from the support material. At least lastly, the peptide is washed with a suitable solvent (step V).

Optionally, pre-swelling (step O) of the solid support material, usually a resin, is carried out at the beginning of the method. According to the invention, at least one of said steps is at least temporarily ultrasound-assisted (X). This is to be understood to mean that, at least temporarily, ultrasound (X) of a frequency of at least than 25 kHz is applied to the reaction medium in which the synthesis takes place. It has been found that an ultrasonic bath in which the reaction medium is introduced by means of a vessel is particularly well suited for transmission. Both preparatively and with respect to the synthesis time, it has further been found to be advantageous if ultrasound (X) acts on the reaction medium over several steps, preferably without switching off between the steps. In particular with regard to steps I to IV, the ultrasound carried out according to the invention can bring about a reduction in the synthesis time in the region of an order of magnitude.

Table 1 compares the synthesis times of the individual steps of the repeat units for a prior art method without ultrasonic action and according to the invention with ultrasonic action in the range of 50 to 150 KHz. It is clear that the method according to the invention is ten times faster than a comparable method without ultrasound.

TABLE 1

| Comparison of the required synthesis times of methods according to the prior art and according to the invention. | | |
|---|---|---|
| Step | Prior art | Method according to the invention |
| Deprotection (Step II) | 3 × 5 min | 2 × 1 min |
| Washing (IV) | 5 × 1 min | 3 × 30 sec |
| Peptide propagation (III) | 2 × 30 min | 2 × 3 min |
| Total | 1 h 20 min | 8 min 30 sec |

In addition to the protecting groups bound to the N- or C-terminus, the amino acids can have further protecting groups to block reactive side chains. Attention must be paid here to the requirements with regard to the chemical and physical environment during peptide synthesis, such as ultrasound and base or acid stability. Suitable protecting groups for reactive side chains for use in the method according to the invention are, for example, acid-labile protecting groups, for example S-2,4,6-trimethoxybenzyl (Tmob), triphenylmethyl (Trt), tert-butyl (tBu), tert-butyloxycarbonyl (Boc) and 2,2,4,6,7-pentamethyldihydrobenzofuran-5-sulfonyl (Pbf).

With reference to the method according to the invention, for example, Fmoc amino acids selected from the following group, which is noted as a single-letter code for the amino acid, are particularly suitable for peptide propagation: Fmoc-A-OH, Fmoc-C(Trt)-OH, Fmoc-D (OtBu)-OH, Fmoc-E (OtBu)-OH, Fmoc-F-OH, Fmoc-G-OH, Fmoc-H (Trt)-OH, Fmoc-I-OH, Fmoc-K(Boc)-OH, Fmoc-L-OH, Fmoc-M-OH, F moc-N(Trt)-OH, Fmoc-P-OH, Fmoc-Q-Trt-OH, Fmoc-R-Pbf-OH, Fmoc-S-tBu-OH, Fmoc-T-tBu-OH, Fmoc-V-OH, Fmoc-W(Boc)-OH, Fmoc-Y-(tBu)-OH, Fmoc-Gln (Tmob)-OH, Fmoc-Asn(Tmob)-OH (TMOB=2, 4,6-trimethoxy-benzyl).

The Fmoc amino acids can be present in both the L and D forms.

With these, the synthesis time could be reduced more than tenfold compared to the prior art without yield losses.

Table 2 shows the typical course of synthesis of the method according to the invention in a preferred embodiment on the basis of a pipetting scheme using the example of endomorphin. This basically comprises the steps mentioned above (O-V), which are, however, described in more detail and with sub-steps in the following example. A first step is the pre-swelling of the resin (O), followed by deprotection of the resin, for example with 20% piperidine in DMF, subsequent washing with a solvent, for example DMF or DCM, coupling of the amino acid (I), washing again with a solvent, for example DMF or DCM, deprotection of the amino acid and finally washing with a solvent, preferably DMF or DCM.

The cycle sequence is always the same here. After the last amino acid (AA) has been coupled, it is deprotected, washed, and rinsed with solvent, for example DMF or DCM. During the individual cycles, ultrasound with frequencies in the range of 25 KHz to 2 MHz acts on the reaction medium in the shown embodiment. In the present example, the ultrasound (X) is also not interrupted between the steps. Alternatively, the ultrasound can be interrupted between the steps or during individual steps. However, in the tested frequencies in the range of 40 kHz to 2 MHz and in particularly in the range of 50 KHz to 200 KHz, continuous ultrasound was shown to be particularly advantageous.

In the example shown, the steps of pre-swelling and final rinsing with solvent, preferably dichloromethane (DCM), are carried out without ultrasound. However, this is only a preferred embodiment, and therefore ultrasound may indeed be provided over all steps.

TABLE 2

| Synthesis sequence of a solid-phase peptide synthesis with the method according to the invention in a preferred embodiment. | | | | | |
|---|---|---|---|---|---|
| | | Pipetting scheme Volume (ml) | t (min) | Repetition | Ultra-sound |
| | 1. AA, Phe, F | | | | |
| 1 | Pre-swelling | 2 | 2 | 2 | no |
| 2 | Deprotection | 1 | 1 | 2 | yes |
| 3 | Washing | 1 | 30 s | 3 | yes |
| 4 | Coupling | F in HCTU, 250 µl DIPEA, 153.3 µl | 3 | 2 | yes |
| 5 | Washing | 1 | 30 s | 3 | yes |
| | 2. AA, Trp, W | | | | |
| 6 | Deprotection | 1 | 1 | 2 | yes |
| 7 | Washing | 1 | 30 s | 3 | yes |
| 8 | Coupling | W in HCTU, 250 µl DIPEA, 153.3 µl | 3 | 2 | yes |
| 9 | Washing | 1 | 30 s | 3 | yes |
| | 3. AA, Pro, P | | | | |
| 10 | Deprotection | 1 | 1 | 2 | yes |
| 11 | Washing | 1 | 30 s | 3 | yes |
| 12 | Coupling | P in HCTU, 250 µl DIPEA, 153.3 µl | 3 | 2 | yes |
| 13 | Washing | 1 | 30 s | 3 | yes |
| | 4. AA, Tyr, Y | | | | |
| 14 | Deprotection | 1 | 1 | 2 | yes |
| 15 | Washing | 1 | 30 s | 3 | yes |
| 16 | Coupling | Y in HCTU, 250 µl DIPEA, 153.3 µl | 3 | 2 | yes |
| 17 | Washing | 1 | 30 s | 3 | yes |
| 18 | Deprotection | 1 | 1 | 2 | yes |
| 19 | Washing | 1 | 30 s | 3 | yes |
| 36 | Flushing with DCM | 1 | 1 | 3 | no |

The method according to the invention can be carried out as a so-called short-term or long-term synthesis. The difference between the two is shown as an example in Table 3:

TABLE 3

| Description of short- and long-term synthesis | |
|---|---|
| Short-term synthesis | Long-term synthesis |
| Deprotection with ultrasound Deprotection duration: 30 s | Deprotection with ultrasound Deprotection duration: 1 min |

TABLE 3-continued

| Description of short- and long-term synthesis | |
|---|---|
| Short-term synthesis | Long-term synthesis |
| Number of deprotection steps: 1 | Number of deprotection steps: 2 |
| Washing without ultrasound | Washing with ultrasound 30 s each |
| Per washing step: wash 5x | Per washing step: wash 3x |
| Single coupling of the AA | Double coupling of the AA |

Short-term synthesis differs from long-term synthesis basically in that the duration of deprotection is halved. Furthermore, the number of washing and deprotection steps is reduced. Despite the fact that the long-term synthesis requires a longer synthesis time, it also provides a reduced synthesis time of one tenth compared to the prior art.

Synthesis Scheme for Double Coupling in Ultrasonic Synthesis (Single Frequency)

TABLE 4

| Step | Chemical | Fmoc-AA | V [ml] | t [min] |
|---|---|---|---|---|
| deprotection suction | 20% piperidine | | 1 | 1 |
| deprotection suction | 20% piperidine | | 1 | 1 |
| washing suction | DMF | | 1 | 0.5 |
| washing suction | DMF | | 1 | 0.5 |
| washing suction | DMF | | 1 | 0.5 |
| addition AA (+HCTU, DIPEA) suction | AA + 1 ml HCTU + 1 ml DIPEA | G | 2 | 3 |
| addition AA (+HCTU, DIPEA) suction | AA + 1 ml HCTU + 1 ml DIPEA | G | 2 | 3 |
| washing suction | DMF | | 1 | 0.5 |
| washing suction | DMF | | 1 | 0.5 |
| washing suction | DMF | | 1 | 0.5 |

Total duration of a cycle with double coupling: 11 min

This cycle is repeated until the entire sequence has been synthesised (example ACP: H-VQAAIDYING-NH2 (SEQ ID NO: 1)→10 amino acids→10 cycles).

The preparatory steps such as pre-swelling and washing, as well as the final washing steps are not listed here.

Synthesis Scheme for Single Coupling in Ultrasonic Synthesis (Single Frequency)

TABLE 5

| Step | Chemical | Fmoc-AA | V [ml] | t [min] |
|---|---|---|---|---|
| deprotection suction | 20% piperidine | | 1 | 1 |
| deprotection suction | 20% piperidine | | 1 | 1 |
| washing suction | DMF | | 1 | 0.5 |
| washing suction | DMF | | 1 | 0.5 |
| washing suction | DMF | | 1 | 0.5 |
| addition AA (+HCTU, DIPEA) suction | AA + 1 ml HCTU + 1 ml DIPEA | G | 2 | 3 |
| washing suction | DMF | | 1 | 0.5 |
| washing suction | DMF | | 1 | 0.5 |
| washing suction | DMF | | 1 | 0.5 |

Total duration of a cycle with single coupling: 8 min

This cycle is repeated until the entire sequence has been synthesised (example ACP: H-VQAAIDYING-NH2 (SEQ ID NO: 1)→10 amino acids→10 cycles).

The preparatory steps such as pre-swelling and washing, as well as the final washing steps are not listed here.

Synthesis Scheme for Single Coupling in Ultrasonic Synthesis (Several Frequencies, for Example 132 kHz and 470 kHz)

TABLE 6

| Step | Chemical | Fmoc-AA | Volume [ml] | Time [min] | Ultra-sound | F [kHz] |
|---|---|---|---|---|---|---|
| deprotection suction | 20% piperidine | | 1 | 2*0.5 | yes | 132 + 470 |
| deprotection suction | 20% piperidine | | 1 | 2*0.5 | yes | 132 + 470 |
| washing suction | DMF | | 1 | 0.5 | yes | 132 |
| washing suction | DMF | | 1 | 0.5 | yes | 132 |
| washing suction | DMF | | 1 | 0.5 | yes | 132 |
| addition AA (+HCTU, DIPEA) suction | AA + 1 ml HCTU + 1 ml DIPEA | I | 2 | 1 + 2 | yes | 132 + 470 |
| washing suction | DMF | | 1 | 0.5 | yes | 132 |
| washing suction | DMF | | 1 | 0.5 | yes | 132 |
| washing suction | DMF | | 1 | 0.5 | yes | 132 |

Deprotection: 2*0.5 yes 132+470→0.5 min at 132 kHz and then 0.5 min at 470 KHz addition AA (+HCTU, DIPEA):

1+2 yes 132+470→1 min at 132 kHz and then 2 min at 470 kHz

Total duration of a cycle with single coupling: 8 min

This cycle is repeated until the entire sequence has been synthesised (example: H-PYLFWLAAI-NH2 (SEQ ID NO: 2)→9 amino acids→9 cycles).

The preparatory steps such as pre-swelling and washing, as well as the final washing steps are not listed here.

Synthesis Scheme for LIPS Synthesis (3-Fold Coupling)

TABLE 7

| Step | Chemical | Time | Number | Total time |
|------|----------|------|--------|------------|
| deprotection suction | 20% piperidine | 2 min | 5 | 10 min |
| washing suction | DMF | 10 sec | 5 | 50 sec |
| addition AA | distribution of the pens | approx.. 20 min | 3 | 105 min |
| activation suction | NMM | 15 min 10 sec | | |
| washing suction | DMF | 10 sec | 3 | 30 sec |
| acetylation suction | capping solution | 2 min | 2 | 4 min |
| washing suction | DMF | 20 sec | 5 | 2 min |

Total duration of a cycle with 3-fold coupling: approx. 122 min

This cycle is repeated until the entire sequence has been synthesised (example: H-VQAAIDYING-NH2 (SEQ ID NO: 1)→10 amino acids→10 cycles).

The time needed to distribute the pens depends on several factors, therefore only approximate values are given here.

Synthesis Scheme for ABI Synthesis (1-Fold Coupling) without Capping (Acetylation)

TABLE 8

| Programme module | Process | Duration (approx. from the manual) | Comment |
|------------------|---------|-----------------------------------|---------|
| B | deprotection | 15 min | 2x at least |
| A | dissolving the amino acid in cartridge | 8 min | |
| D | washing | 2.5 min | duration varies depending on the number of cycles performed 5x at least |
| E | transfer of the dissolved amino acid into reaction vessel | 2.1 min | |
| F | coupling | 15 min | |
| D | washing | 2.5 min | duration varies depending on the number of cycles performed 5x at least |

Total duration of a cycle with 1-fold coupling: approx. 80 min.

The times can only be given with approximate values, as the individual modules can have different lengths, which in turn depends on the sequence to be synthesised. In addition, internal sensors measure the proportion of deprotected Fmoc groups during deprotection.

This cycle is repeated until the entire sequence has been synthesised (example: H-VQAAIDYING-NH2 (SEQ ID NO: 1)→10 amino acids→10 cycles).

Within the modules, additional washing steps are included, and therefore these are not shown separately.

Synthesis Scheme for ABI Synthesis (2-Fold Coupling) with Capping (Acetylation)

TABLE 9

| Programme module | Process | Duration (approx. from the manual) | Comment |
|------------------|---------|-----------------------------------|---------|
| B | deprotection | 15 min | 2x at least |
| A | dissolving the amino acid in cartridge | 8 min | |
| D | wash | 2.5 min | duration varies depending on the number of cycles performed 5x at least |
| E | transfer of the dissolved amino acid into reaction vessel | 2.1 min | |
| A | dissolving the amino acid in cartridge | 8 min | |
| D | wash | 2.5 min | duration varies depending on the number of cycles performed 5x at least |
| E | transfer of the dissolved amino acid into reaction vessel | 2.1 min | 2x |
| F | coupling | 15 min | 2x |
| C | capping | 9.5 min | |
| D | wash | 2.5 min | duration varies depending on the number of cycles performed 5x at least |

Total duration of a cycle with 2-fold coupling: approx. 130 min.

The times can only be given with approximate values, as the individual modules can have different lengths, which in turn depends on the sequence to be synthesised. In addition, internal sensors measure the proportion of deprotected Fmoc groups during deprotection.

This cycle is repeated until the entire sequence has been synthesised (example: H-VQAAIDYING-NH2 (SEQ ID NO: 1)→10 amino acids→10 cycles.

Within the modules, additional washing steps are included; these are not shown separately.

ACP H-VQAAIDYING-NH2 (SEQ ID NO: 1) M=1063.2 Da

Synthesis scale: 25 μmol

Synthetic resin: Knorr Amid Resin LS 1% DVB

Activator: HCTU

Base: DIPEA

| Amino acids used: | |
|-------------------|---|
| Amino acid (L-amino acids) | Permanent protecting group |
| Fmoc-Ala-OH | — |
| Fmoc-Asp(tBu)-OH | Tert. Butyl |
| Fmoc-Gly-OH | — |
| Fmoc-Ile-OH | — |
| Fmoc-Asn(Trt)-OH | Trityl |
| Fmoc-Gln(Trt)-OH | Trityl |

-continued

| Amino acids used: | |
| --- | --- |
| Amino acid (L-amino acids) | Permanent protecting group |
| Fmoc-Val-OH | — |
| Fmoc-Tyr(tBu)-OH | Tert. Butyl |

Ratio of free amino function resin:aminoacid:activator: base; 1:4:3.9:8

Figure 11:
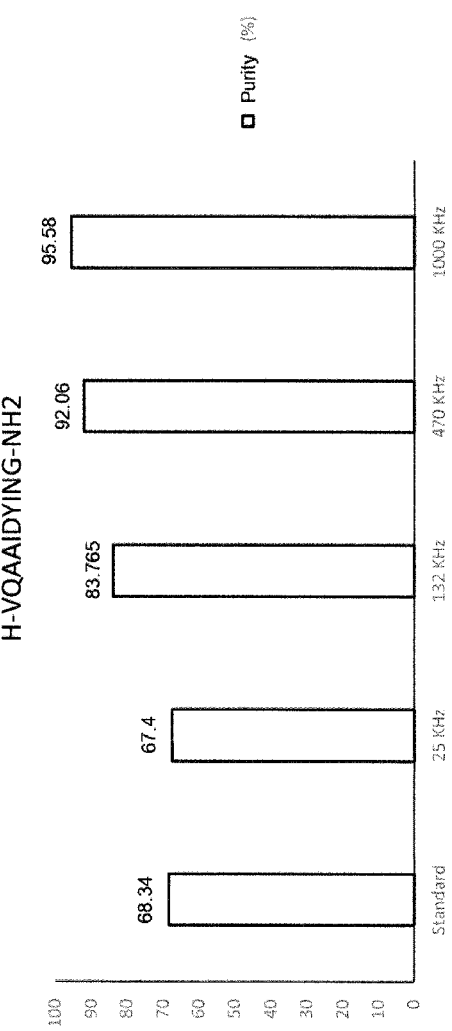

FIG. 11 compares the average synthesis quality of the ACP peptide H-VQAAIDYING-NH$_2$ (SEQ ID NO: 1), taking into account the synthesis strategy:

660-SL3 LIPS: ACP in microtiter plate (MTP) LIPS robot 3-fold coupling
(standard protocol) duration: 22.5 h
USPS 132 KHz 50% power: ACP in ultrasound, 132 kHz 1-fold coupling (average of 2 batches) duration: 2.5 h
USPS 470 KHz 50% power: ACP in ultrasound, 470 kHz 1-fold coupling (average of 2 batches) duration: 2.5 h
USPS 1000 KHz 60% power: ACP in ultrasound, 1000 KHz 1-fold coupling (average of 2 batches) duration. 2.5 h It can be seen that the level of frequency increases the product quality.

Figure 12:
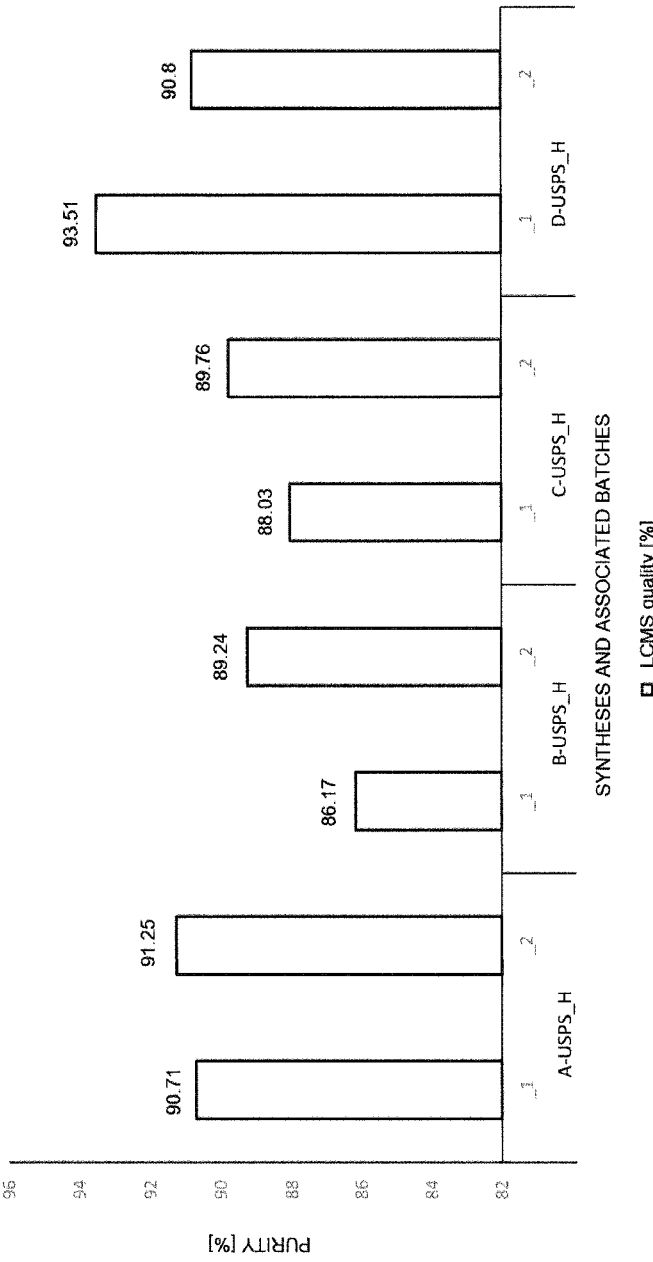

FIG. 12 shows graphically the qualities of the syntheses of H-VQAAIDYING-NH$_2$ (SEQ ID NO: 1) 25 μmol according to FIG. 11.

| Batch number | Fre-quency [kHz] | Ultrasound power [%] | Ultrasound during washing ? | Ultrasound during deprotection? | Ultrasound during coupling? | Coupling number |
| --- | --- | --- | --- | --- | --- | --- |
| A-USPS_H_1 | 132 | 50 | yes | yes | yes | 2 |
| A-USPS_H_2 | 132 | 50 | yes | yes | yes | 2 |
| B-USPS_H_1 | 132 | 50 | no | yes | yes | 2 |
| B-USPS_H_2 | 132 | 50 | no | yes | yes | 2 |
| C-USPS_H_1 | 132 | 50 | no | no | yes | 2 |
| C-USPS_H_2 | 132 | 50 | no | no | yes | 2 |
| D-USPS_H_1 | 470 | 100 | yes | yes | yes | 2 |
| D-USPS_H_2 | 470 | 100 | yes | yes | yes | 2 |

As a result, it can be stated that a permanent sounding increases the product quality and that an increase in frequency also increases the product quality.

Figure 13:
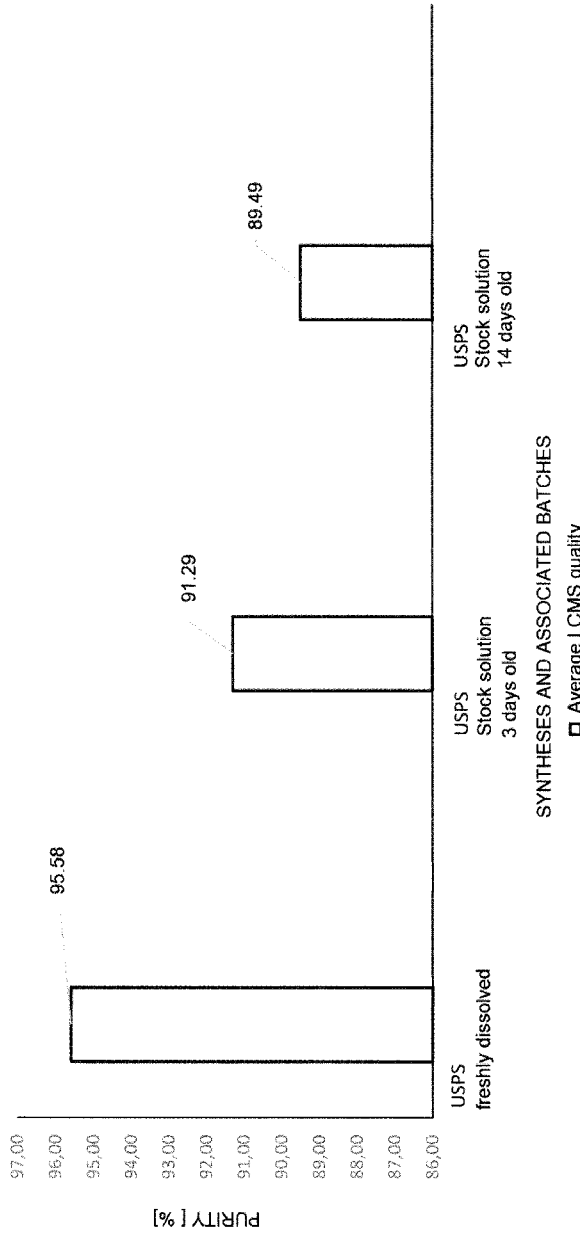

FIG. 13 shows the testing of stock solutions on amino acids of different solution durations. With the different stock solutions, syntheses of the ACP peptide are carried out using ultrasound at 1000 KHz with different solution times for the amino acids used.

It can be seen that a shorter dissolution time of the amino acids used increases the product quality.

Figure 14:
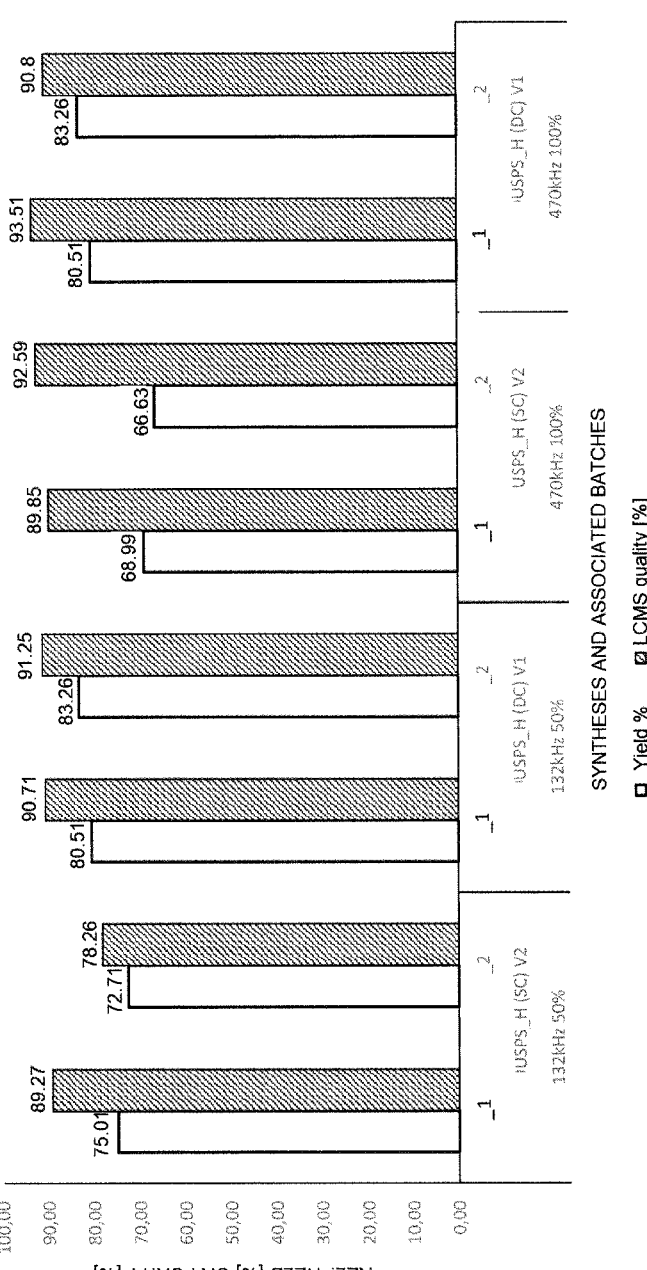

FIG. 14 is a graphical representation of the comparison of yield and quality in terms of coupling number at different frequencies H-VQAAID (SEQ ID NO: 3).

| Synthesis number (number of approaches) | Coupling number | Frequency ultrasound |
| --- | --- | --- |
| USPS_H (2) | 1 | 132 kHz 50% |
| USPS_H (2) | 2 | 132 kHz 50% |
| USPS_H (2) | 1 | 470 kHz 100% |
| USPS_H (2) | 2 | 470 kHz 100% |

It can be seen that at low frequencies (132 kHz) the LCMS quality increases with an increase in the coupling number.

At high frequencies (470 kHz) there is hardly any difference in the LCMS quality.

Frequency-independently, however, the yield increases with an increase in the coupling number.

For the experiment (FIG. 15), a different peptide is chosen than for the previous tests. The sequence is PYLFWLAAI-NH2 (SEQ ID NO: 2)

This is also a difficult peptide to synthesise.

ACP H-PYLFWLAAI-NH2 (SEQ ID NO: 2) M=1092.6 Da

Synthesis scale: 25 μmol
Synthetic resin: Knorr Amid Resin LS 1% DVB
Activator: HCTU
Base: DIPEA

| Amino acids used: | |
| --- | --- |
| Amino acid (L-amino acids) | Permanent protection group |
| Fmoc-Ala-OH | — |
| Fmoc-Phe-OH | — |
| Fmoc-Ile-OH | — |
| Fmoc-Leu-OH | — |
| Fmoc-Pro-OH | — |
| Fmoc-Trp(Boc)-OH | Butyloxycarbonyl |
| Fmoc-Tyr(tBu)-OH | Tert. Butyl |

Ratio of free amino function resin:aminoacid:activator: base; 1:4:3.9:8

Figure 15:
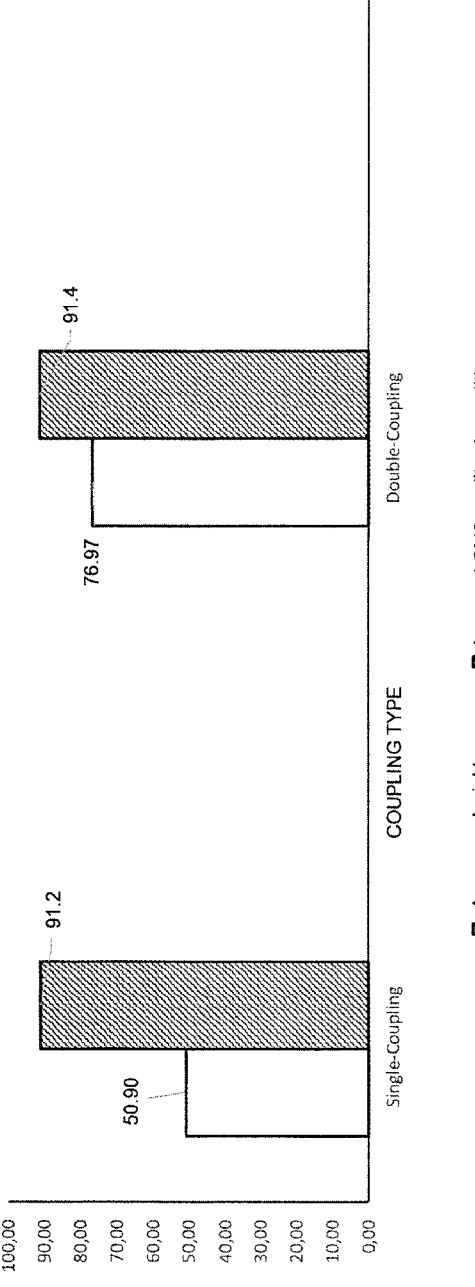

FIG. 15 shows graphically the comparison of single and double coupling and amino acid excess for this peptide.

| Synthesis number (number of batches) | Coupling number | Frequency ultrasound |
| --- | --- | --- |
| 150819USPS_H (2) | 1 (single coupling) | 470 kHz 50% |
| 241019USPS_H (2) | 2 (double Coupling) | 470 kHz 50% |

At the same frequency, there is no significant difference in terms of synthesis quality.

When the coupling number is increased, however, there is a clear increase in the relative yield.

Figure 16:
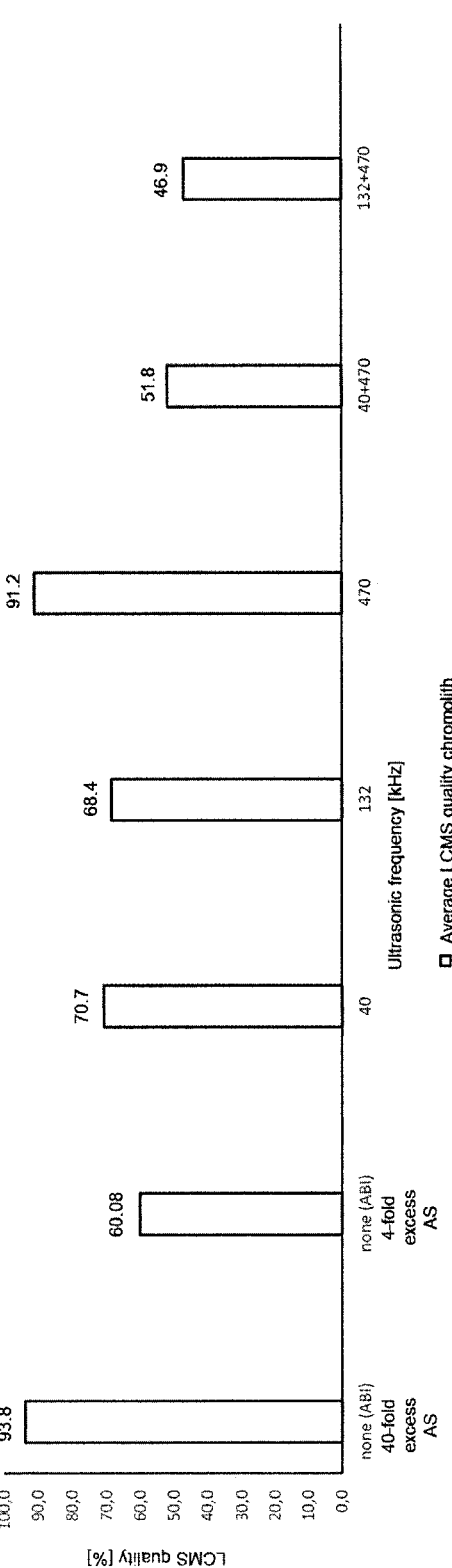

FIG. 16 shows a graphical representation of the comparison of the average synthesis quality of a peptide using different ultrasonic frequencies.

Shown are the syntheses of the peptide PYLFWLAAI-NH2 (SEQ ID NO: 2), which were synthesised using single coupling at different ultrasonic frequencies.

Without ultrasound:
Conventional ABI synthesis with 40-fold excess of amino acid.
Conventional ABI synthesis with 4-fold excess of amino acid.

The lower the excess of amino acid, the poorer the LCMS quality in a conventional ABI synthesis.

Simple Ultrasonic Frequencies 4-Fold Excess of Amino Acid

Frequencies: 40 kHz, 132 KHz, 470 KHz

With increasing frequency, the LCMS quality increases.

Coupled Ultrasonic Frequencies (Deprotection, Coupling), Washing Exclusively at Lower Frequency Coupled frequencies: 40 KHz+470 KHz and 132 KHz+470 KHz Switching between frequencies leads to a significant deterioration of the synthesis quality.

Ultrasound Vs. Conventional ABI Synthesis

To achieve good to very good LCMS quality in conventional ABI synthesis, very high excesses of amino acid are necessary (40-fold).

With the help of ultrasound, a 4-fold excess of amino acid is sufficient. Here, the higher the frequency used, the higher the LCMS quality.

Equivalent results showed the following parameters:

ABI (40× excess) and 470 kHz (4× excess).

By means of the ultrasonic synthesis, at least equivalent and usually better results can be achieved in a shorter time and with reduced use of solvents and amino acids.

Figure 8:
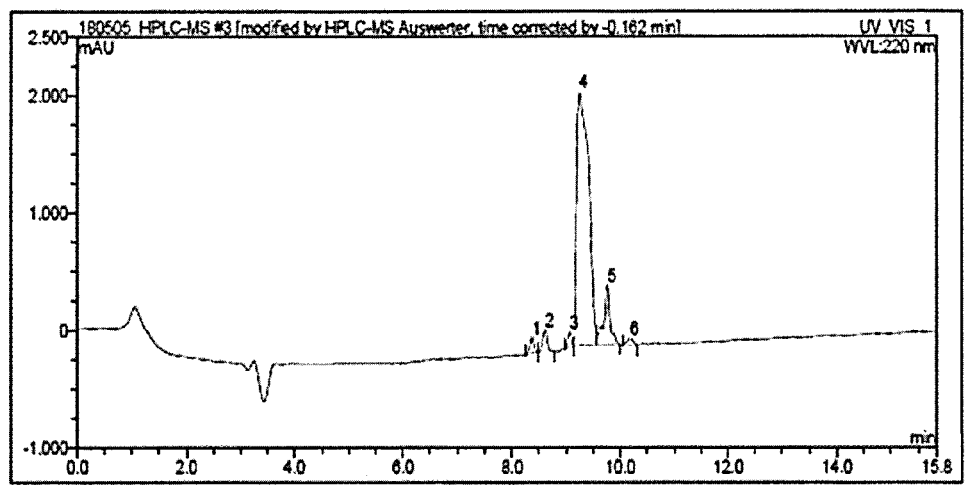
Figure 9:
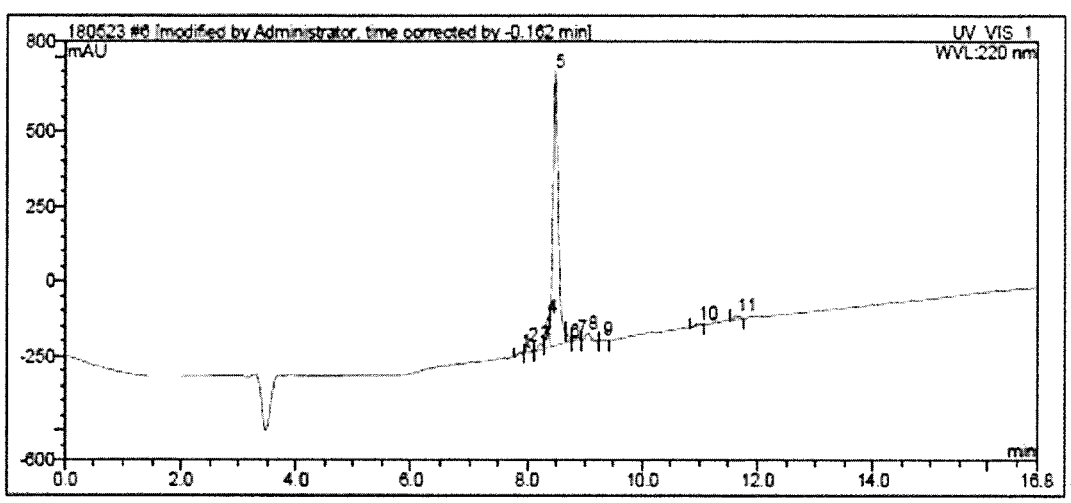
Figure 10:
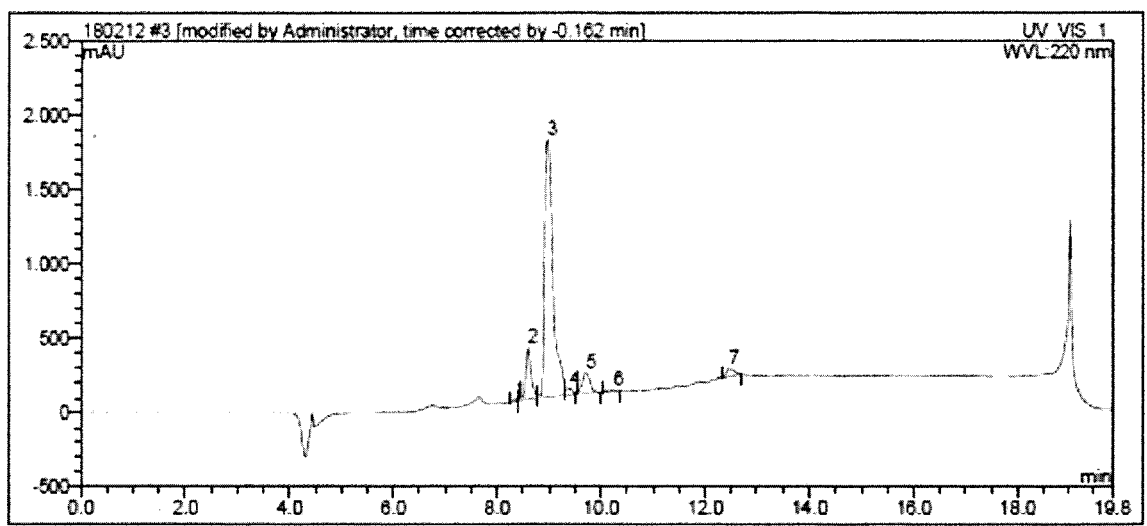

FIGS. 8 to 10 each show the composition of a peptide synthesised by solid-phase peptide synthesis. The peptides shown in FIGS. 8 to 9 were produced by means of the method according to the invention, while FIG. 10 is based on a peptide synthesised according to the prior art by means of Tetras. All methods were carried out with the device according to the invention.

The products obtained from the various methods were separated by HPLC and the individual peaks were assigned by mass spectrometry and UV-vis spectrometry. Equipment with the following parameters was used:

HPLC MS System

Dionex Binary HPLC Pump

Running medium A: water plus 0.1% formic acid

Running medium B: acetonitrile plus 0.1% formic acid

Flow: 0.5 ml/min

Gilson autosampler for up to 4 microtiter plates

Dionex column oven

Temperature: 30° C.

Dionex UV detector

Measurement at 220 nm

Dionex/Thermo Finnigan Surveyor MSQ Single Quadrupole Mass Spectrometer

Ionisation mode: ESI

Sample temperature: 350° C.

Cone voltage: 50 V

HPLC separation column: Merk, Chromolith WP300, RP18, 100-4.6 mm

| Time (min) | % Running medium B |
|---|---|
| 0 | 5 |
| 2 | 5 |
| 12 | 100 |
| 14 | 100 |
| 15 | 5 |

FIG. 8 shows that the above-mentioned protecting groups for blocking the reactive side chains are stable in the method according to the invention. For this purpose, the results of a peptide synthesis according to the method of the invention are shown for three of the most common protecting groups.

FIG. 8 shows the analysis results of an endomorphin synthesis carried out according to the method of the invention on the basis of the long-term synthesis procedure. Theoretical considerations initially suggested that the oxidation-sensitive tryptophan could be oxidised by the ultrasound during the synthesis. However, this was not confirmed. Rather, the synthesis was successful with a purity of 83%. Only a few by-products were identified.

Methionine, trityl and Tmob protecting groups also proved stable during the method according to the invention in individual tests.

FIG. 9 shows the synthesis of the acyl carrier protein (ACP) with the sequence VQAAIDYING-OH (SEQ ID NO: 1), produced according to the method of the invention with a long-term synthesis.

The protecting groups Fmoc-Q (Tmob)-OH and Fmoc-N (Tmob)-OH were used. The synthesised peptide is basically very difficult to prepare due to its strongly hydrophobic character. Nevertheless, it was possible to produce it with a purity of 82% by means of the method according to the invention. Compared to the synthesis of the same peptide with the prior art Tetras method shown in FIG. 10, where only a purity of 79% could be achieved, it can be seen that the method according to the invention can, among other things, achieve an improvement in yields. In addition, the synthesis time of the peptide produced by the method according to the invention was completed in 2.5 h, whereas the comparative method according to the prior art required 25 h. The method according to the invention is thus ten times shorter.

The use of the method according to the invention and the device according to the invention advantageously lead to a reduction of the synthesis time to a maximum of one tenth of the synthesis time for methods according to the prior art without microwave support. It could be shown that this in no way coincides with a reduction of the yield, rather it could be shown in a direct comparison with a standard method that the method according to the invention produced a higher purity of the target peptide, in particular when using the device according to the invention.

LIST OF REFERENCE SIGNS

1 Synthesis device
2 Gripper arm
3 Working region
4 Holder
5 Synthesis plate
6 Valve block
7 Suction pump
8 Rinsing comb
9 Reaction chambers
10 Rinsing agent supply line
11 Synthesis pen
12 Main body, hollow cylinder
13, 13*a* Closure, screw closure, movable lid with bayonet closure
13*b* Locking bayonet closure
14 Mouthpiece
15 Valve needle
16 Stop valve
17 Piston rod
18 Piston
19 Compression spring
20 Synthesis building block
21 Inert gas
23 Outlet opening 25 Permeable material/frit
26 Solid phase
27 Sample plate
28 Membrane
29 Seal
30 Gripper arm receptacle
31 Dosing cylinder
32 Outlet valve
33 Return spring
33*a* Fastening for return spring
33*b* Return spring, screw grub fastening
34 Gap for cylinder filling
35 Union nut
36 Dosing cannula guide
37 Dosing cannula
50 Ultrasonic bath
O Pre-swelling
I Binding of an amino acid protected at the N-terminus by a protecting group to a solid support material via a C-terminus of the amino acid,
II Splitting-off of the protecting group
III Performing at least one peptide propagation
IV Termination of the reaction by splitting off the peptide from the support material
V Washing
X Ultrasound action

The invention claimed is:

1. A method for carrying out solid-phase peptide synthesis comprising the steps of:
   a) binding an amino acid protected at the N-terminus by a protecting group to a solid support material via a C-terminus of the amino acid,
   b) splitting off the protecting group,
   c) performing at least one peptide propagation, and
   d) terminating the reaction by splitting off the peptide from the support material, wherein steps a) to d) take place in a liquid reaction medium, and at least during one of the steps, ultrasound with a frequency in the range of 25-100 to 2000 kHz acts at least intermittently on the reaction medium.

2. The method according to claim 1, wherein the ultrasound acts on the reaction medium with a frequency in the range of more than 110 kHz.

3. The method according to claim 1, wherein the ultrasound acts on the reaction medium with a frequency in the range of not more than 1000 kHz.

4. The method according to claim 1, wherein the ultrasound is transmitted to the reaction medium via an external liquid bath.

5. The method according to claim 4, wherein the ultrasonic bath is controlled to a temperature range of from 20° C. to 100° C.

---

```
                    SEQUENCE LISTING

<160> NUMBER OF SEQ ID NOS: 3

<210> SEQ ID NO 1
<211> LENGTH: 10
<212> TYPE: PRT
<213> ORGANISM: Artificial sequence
<220> FEATURE:
<223> OTHER INFORMATION: Example peptide sequence used to illustrate
      synthesis cycles

<400> SEQUENCE: 1

Val Gln Ala Ala Ile Asp Tyr Ile Asn Gly
1               5                   10

<210> SEQ ID NO 2
<211> LENGTH: 9
<212> TYPE: PRT
<213> ORGANISM: Artificial sequence
<220> FEATURE:
<223> OTHER INFORMATION: Example peptide sequence used to illustrate
      synthesis cycles

<400> SEQUENCE: 2

Pro Tyr Leu Phe Trp Leu Ala Ala Ile
1               5

<210> SEQ ID NO 3
<211> LENGTH: 6
<212> TYPE: PRT
<213> ORGANISM: Artificial sequence
<220> FEATURE:
<223> OTHER INFORMATION: Fragment used in connection with Fig 14
      yield/quality comparison

<400> SEQUENCE: 3

Val Gln Ala Ala Ile Asp
1               5
```

6. The method according to claim 5, wherein the temperature range is from 20° C. to 70° C.

7. The method according to claim 5, wherein the temperature range is from 40° C. to 60° C.

8. The method according to claim 1, further comprising a washing step $W_b$) taking place after step b), a washing step $W_c$) taking place after step c) and/or a washing step $W_a$) taking place after step d), wherein ultrasound also acts on the reaction medium during at least one of these steps.

9. The method according to claim 8, wherein during all steps a) to d) and/or $W_b$), $W_c$) and $W_a$) ultrasound acts on the reaction medium without interruption and/or with the same frequency.

10. The method according to claim 8, wherein when ultrasound acts on the reaction medium in several steps, the ultrasonic frequency varies between the steps.

11. The method according to claim 10, wherein the ultrasonic frequency varies between reaction steps a) to d) and washing steps $W_{b-d}$).

12. The method according to claim 8, wherein the frequency during at least one of the washing steps is more than 100 kHz.

13. The method according to claim 12, wherein the frequency during at least one of the washing steps is more than 110 kHz.

14. The method according to claim 1, wherein the amino acid is protected at the N-terminus by a base-labile protecting group.

15. The method according to claim 14, wherein the base-labile protecting group is optionally split off by using a secondary amine.

16. The method according to claim 15, wherein the secondary amine is fluorenylmethoxycarbonyl (Fmoc).

17. The method according to claim 14, wherein the base-labile protecting group is split off by using a secondary amine.

18. The method according to claim 17, wherein the secondary amine is fluorenylmethoxycarbonyl (Fmoc).

19. The method according claim 1, wherein the amino acid comprises a protecting group for protecting a side chain.

20. The method according to claim 19, wherein the protecting group is selected from a group consisting of S-2,4,6-trimethoxybenzyl (Tmob), triphenylmethyl (Trt), tert-butyl (tBu), tert-butyloxycarbonyl (Boc), and 2,2,4,6,7-pentamethyldihydrobenzofuran-5-sulfonyl (Pbf).

21. The method according to claim 1, wherein ultrasound acts on the reaction medium in only one step.

22. The method according to claim 1, wherein the method is carried out semi-automated/automated and/or in parallel.

23. The method according to claim 22, wherein step d) comprises a dosing step, a washing step and a filtering step, and in the case of semi-automated performance, the dosing step is performed manually, and the further steps are performed in automated performance.

24. The method according to claim 1, wherein the ultrasound acts on the reaction medium with a frequency in the range of not more than 500 kHz.

25. The method according to claim 1, wherein ultrasound acts on the reaction medium in only step c).

26. Automated parallel solid-phase peptide synthesis comprising a method according to claim 1.

27. A peptide produced by a method according to claim 1.

\* \* \* \* \*